(12) United States Patent
Wallace et al.

(10) Patent No.: US 8,555,882 B2
(45) Date of Patent: Oct. 15, 2013

(54) VENTILATOR BREATH DISPLAY AND GRAPHIC USER INTERFACE

(75) Inventors: Charles L. Wallace, Encinitas, CA (US); Warren G. Sanborn, Escondido, CA (US); David Arnett, Half Moon Bay, CA (US); Jay Butterbrodt, Lawrenceburg, IN (US); Howard L. Ferguson, Elk, WA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/549,941

(22) Filed: Jul. 16, 2012

(65) Prior Publication Data

US 2012/0279501 A1 Nov. 8, 2012

Related U.S. Application Data

(63) Continuation of application No. 13/163,531, filed on Jun. 17, 2011, which is a continuation of application No. 11/856,632, filed on Sep. 17, 2007, now Pat. No. 8,001,967, which is a continuation of application No. 11/366,259, filed on Mar. 2, 2006, now Pat. No. 7,270,126, which is a continuation of application No. 10/733,794, filed on Dec. 10, 2003, now Pat. No. 7,036,504, which is a continuation of application No. 09/882,200, filed on Jun. 15, 2001, now Pat. No. 6,675,801, which is a continuation of application No. 09/253,387, filed on Feb. 19, 1999, now Pat. No. 6,269,812, which is a continuation of application No. 08/818,807, filed on Mar. 14, 1997, now Pat. No. 5,881,723.

(51) Int. Cl.
*F16K 31/02* (2006.01)
*A62B 7/00* (2006.01)
*A62B 9/00* (2006.01)

(52) U.S. Cl.
USPC .................................. 128/204.21; 128/205.23

(58) Field of Classification Search
USPC ............. 128/202.22, 204.18, 204.21, 204.23, 128/205.23; 345/440–440.2; 715/771; 600/529
See application file for complete search history.

(56) References Cited

U.S. PATENT DOCUMENTS 3,577,984 A    5/1971    Levy et al.
3,659,590 A    5/1972    Jones et al.
3,871,371 A    3/1975    Weigl (Continued)

FOREIGN PATENT DOCUMENTS

EP    0274996    7/1988
EP    0414777    3/1991

(Continued)

OTHER PUBLICATIONS

US 7,284,551, 10/2007, Jones et al. (withdrawn).

(Continued)

*Primary Examiner* — Kristen Matter

(57) ABSTRACT

A ventilation control system for controlling the ventilation of a patient. The ventilation control system utilizes a user-friendly user interface for the display of patient data and ventilator status. The user interface includes a graphic representation of a breath cycle that displays the breath cycle currently being ventilated, and is also responsive to changes in ventilation settings to assist the user in evaluating the effect of those changes on the ventilator strategy before the changes are implemented.

20 Claims, 9 Drawing Sheets

(56) References Cited

U.S. PATENT DOCUMENTS

| | | | |
|---|---|---|---|
| 3,940,742 A | 2/1976 | Hudspeth et al. | |
| 3,961,624 A | 6/1976 | Weigl | |
| 3,961,627 A | 6/1976 | Ernst et al. | |
| 3,977,394 A | 8/1976 | Jones et al. | |
| 3,991,304 A | 11/1976 | Hillsman | |
| 3,996,928 A | 12/1976 | Marx | |
| 4,034,743 A | 7/1977 | Greenwood et al. | |
| 4,036,217 A | 7/1977 | Ito et al. | |
| 4,053,951 A | 10/1977 | Hudspeth et al. | |
| 4,090,513 A | 5/1978 | Togawa | |
| 4,112,931 A | 9/1978 | Burns | |
| 4,187,842 A | 2/1980 | Schreiber | |
| 4,215,409 A | 7/1980 | Strowe | |
| 4,241,739 A | 12/1980 | Elson | |
| 4,258,718 A | 3/1981 | Goldman | |
| 4,296,756 A | 10/1981 | Dunning et al. | |
| 4,308,872 A | 1/1982 | Watson et al. | |
| 4,323,064 A | 4/1982 | Hoenig et al. | |
| 4,326,513 A | 4/1982 | Schulz et al. | |
| 4,391,283 A | 7/1983 | Sharpless et al. | |
| 4,401,115 A | 8/1983 | Monnier | |
| 4,401,116 A | 8/1983 | Fry et al. | |
| 4,407,295 A | 10/1983 | Steuer et al. | |
| 4,440,177 A | 4/1984 | Anderson et al. | |
| 4,444,201 A | 4/1984 | Itoh | |
| 4,463,764 A | 8/1984 | Anderson et al. | |
| 4,473,081 A | 9/1984 | Dioguardi et al. | |
| 4,495,944 A | 1/1985 | Brisson et al. | |
| 4,537,190 A | 8/1985 | Caillot et al. | |
| 4,550,726 A | 11/1985 | McEwen | |
| 4,579,115 A | 4/1986 | Wallroth et al. | |
| 4,637,385 A | 1/1987 | Rusz | |
| 4,654,029 A | 3/1987 | D'Antonio | |
| 4,681,099 A * | 7/1987 | Sato et al. | 128/204.23 |
| 4,736,750 A | 4/1988 | Valdespino et al. | |
| 4,752,089 A | 6/1988 | Carter | |
| 4,790,327 A | 12/1988 | Despotis | |
| 4,796,639 A | 1/1989 | Snow et al. | |
| 4,813,409 A | 3/1989 | Ismach | |
| 4,852,582 A | 8/1989 | Pell | |
| 4,867,152 A | 9/1989 | Kou et al. | |
| 4,876,903 A | 10/1989 | Budinger | |
| 4,917,108 A | 4/1990 | Mault | |
| 4,921,642 A | 5/1990 | LaTorraca | |
| 4,954,799 A | 9/1990 | Kumar | |
| 4,984,158 A | 1/1991 | Hillsman | |
| 4,990,894 A | 2/1991 | Loescher et al. | |
| 5,003,985 A | 4/1991 | White et al. | |
| 5,004,472 A | 4/1991 | Wallace | |
| 5,009,662 A | 4/1991 | Wallace et al. | |
| 5,020,527 A | 6/1991 | Dessertine | |
| 5,021,046 A | 6/1991 | Wallace | |
| 5,057,822 A | 10/1991 | Hoffman | |
| 5,058,601 A | 10/1991 | Riker | |
| 5,072,737 A | 12/1991 | Goulding | |
| 5,097,424 A | 3/1992 | Ginevri et al. | |
| 5,107,831 A | 4/1992 | Halpern et al. | |
| 5,137,026 A | 8/1992 | Waterson et al. | |
| 5,150,291 A | 9/1992 | Cummings et al. | |
| 5,161,525 A | 11/1992 | Kimm et al. | |
| 5,163,423 A | 11/1992 | Suzuki | |
| 5,167,506 A | 12/1992 | Kilis et al. | |
| 5,203,343 A | 4/1993 | Axe et al. | |
| 5,224,487 A | 7/1993 | Bellofatto et al. | |
| 5,231,981 A * | 8/1993 | Schreiber et al. | 128/205.23 |
| 5,235,973 A | 8/1993 | Levinson | |
| 5,237,987 A | 8/1993 | Anderson et al. | |
| 5,246,010 A | 9/1993 | Gazzara et al. | |
| 5,247,434 A | 9/1993 | Peterson et al. | |
| 5,251,632 A | 10/1993 | Delpy | |
| 5,261,397 A | 11/1993 | Grunstein | |
| 5,261,415 A | 11/1993 | Dussault | |
| 5,262,944 A | 11/1993 | Weisner et al. | |
| 5,271,389 A | 12/1993 | Isaza et al. | |
| 5,277,195 A | 1/1994 | Williams | |
| 5,279,304 A | 1/1994 | Einhorn et al. | |
| 5,279,549 A | 1/1994 | Ranford | |
| 5,293,875 A | 3/1994 | Stone | |
| 5,299,568 A | 4/1994 | Forare et al. | |
| 5,301,921 A | 4/1994 | Kumar | |
| 5,303,698 A | 4/1994 | Tobia et al. | |
| 5,303,699 A | 4/1994 | Bonassa et al. | |
| 5,307,795 A | 5/1994 | Whitwam et al. | |
| 5,319,355 A | 6/1994 | Russek | |
| 5,319,540 A | 6/1994 | Isaza et al. | |
| 5,325,861 A | 7/1994 | Goulding | |
| 5,333,106 A | 7/1994 | Lanpher et al. | |
| 5,333,606 A | 8/1994 | Schneider et al. | |
| 5,339,807 A | 8/1994 | Carter | |
| 5,339,825 A | 8/1994 | McNaughton et al. | |
| 5,343,857 A | 9/1994 | Schneider et al. | |
| 5,351,522 A | 10/1994 | Lura | |
| 5,355,893 A | 10/1994 | Mick et al. | |
| 5,357,946 A | 10/1994 | Kee et al. | |
| 5,357,975 A | 10/1994 | Kraemer et al. | |
| 5,363,842 A | 11/1994 | Mishelevich et al. | |
| 5,365,922 A | 11/1994 | Raemer | |
| 5,368,019 A | 11/1994 | LaTorraca | |
| 5,373,851 A | 12/1994 | Reinhold, Jr. et al. | |
| 5,383,449 A | 1/1995 | Forare et al. | |
| 5,383,470 A | 1/1995 | Kolbly | |
| 5,385,142 A | 1/1995 | Brady et al. | |
| 5,390,666 A | 2/1995 | Kimm et al. | |
| 5,401,135 A | 3/1995 | Stoen et al. | |
| 5,402,796 A | 4/1995 | Packer et al. | |
| 5,404,871 A | 4/1995 | Goodman et al. | |
| 5,407,174 A | 4/1995 | Kumar | |
| 5,413,110 A | 5/1995 | Cummings et al. | |
| 5,438,980 A | 8/1995 | Phillips | |
| 5,442,940 A | 8/1995 | Secker et al. | |
| 5,443,075 A | 8/1995 | Holscher | |
| 5,445,160 A | 8/1995 | Culver et al. | |
| 5,446,449 A | 8/1995 | Lhomer et al. | |
| 5,448,996 A | 9/1995 | Bellin et al. | |
| 5,452,714 A | 9/1995 | Anderson et al. | |
| 5,456,264 A | 10/1995 | Series et al. | |
| 5,464,410 A | 11/1995 | Skeens et al. | |
| 5,479,939 A | 1/1996 | Ogino | |
| 5,487,731 A | 1/1996 | Denton | |
| 5,495,848 A | 3/1996 | Aylsworth et al. | |
| 5,501,231 A | 3/1996 | Kaish | |
| 5,507,291 A | 4/1996 | Stirbl et al. | |
| 5,513,631 A | 5/1996 | McWilliams | |
| 5,517,983 A | 5/1996 | Deighan et al. | |
| 5,517,985 A | 5/1996 | Kirk et al. | |
| 5,518,002 A | 5/1996 | Wolf et al. | |
| 5,520,071 A | 5/1996 | Jones | |
| 5,524,615 A | 6/1996 | Power | |
| 5,531,221 A | 7/1996 | Power | |
| 5,534,851 A * | 7/1996 | Russek | 340/573.4 |
| 5,537,992 A | 7/1996 | Bjoernstijerna et al. | |
| 5,542,410 A | 8/1996 | Goodman et al. | |
| 5,542,415 A | 8/1996 | Brady | |
| 5,544,674 A | 8/1996 | Kelly | |
| 5,549,106 A | 8/1996 | Gruenke et al. | |
| 5,549,117 A | 8/1996 | Tacklind et al. | |
| 5,553,620 A | 9/1996 | Snider et al. | |
| 5,558,086 A | 9/1996 | Smith et al. | |
| 5,560,353 A | 10/1996 | Willemot et al. | |
| 5,564,414 A | 10/1996 | Walker et al. | |
| 5,564,432 A | 10/1996 | Thomson | |
| 5,571,142 A | 11/1996 | Brown et al. | |
| 5,575,283 A | 11/1996 | Sjoestrand | |
| 5,582,167 A | 12/1996 | Joseph | |
| 5,590,648 A | 1/1997 | Mitchell et al. | |
| 5,591,130 A | 1/1997 | Denton | |
| 5,596,984 A | 1/1997 | O'Mahoney et al. | |
| 5,598,838 A | 2/1997 | Servidio et al. | |
| 5,606,976 A | 3/1997 | Marshall et al. | |
| 5,611,335 A | 3/1997 | Makhoul et al. | |
| 5,626,144 A | 5/1997 | Tacklind et al. | |
| 5,630,411 A | 5/1997 | Holscher | |
| 5,632,270 A | 5/1997 | O'Mahoney et al. | |
| 5,632,281 A | 5/1997 | Rayburn | |

(56) References Cited

U.S. PATENT DOCUMENTS

| | | |
|---|---|---|
| 5,634,461 A | 6/1997 | Faithfull et al. |
| 5,634,471 A | 6/1997 | Fairfax et al. |
| 5,642,735 A | 7/1997 | Kolbly |
| 5,645,048 A | 7/1997 | Brodsky et al. |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,687,717 A | 11/1997 | Halpern et al. |
| 5,692,497 A | 12/1997 | Schnitzer et al. |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,715,812 A | 2/1998 | Deighan et al. |
| 5,724,990 A | 3/1998 | Ogino |
| 5,730,140 A | 3/1998 | Fitch |
| 5,730,145 A | 3/1998 | Defares et al. |
| 5,735,287 A | 4/1998 | Thomson |
| 5,738,092 A | 4/1998 | Mock et al. |
| 5,740,792 A | 4/1998 | Ashley et al. |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,762,480 A | 6/1998 | Adahan |
| 5,771,884 A | 6/1998 | Yarnall et al. |
| 5,778,874 A | 7/1998 | Maguire et al. |
| 5,791,339 A | 8/1998 | Winter |
| 5,794,612 A | 8/1998 | Wachter et al. |
| 5,794,986 A | 8/1998 | Gansel et al. |
| 5,800,361 A | 9/1998 | Rayburn |
| 5,806,514 A | 9/1998 | Mock et al. |
| 5,809,997 A | 9/1998 | Wolf |
| 5,813,397 A | 9/1998 | Goodman et al. |
| 5,813,399 A | 9/1998 | Isaza et al. |
| 5,819,723 A | 10/1998 | Joseph |
| 5,822,715 A | 10/1998 | Worthington et al. |
| 5,826,570 A | 10/1998 | Goodman et al. |
| 5,826,575 A | 10/1998 | Lall |
| 5,827,179 A | 10/1998 | Lichter et al. |
| 5,829,441 A | 11/1998 | Kidd et al. |
| 5,839,430 A | 11/1998 | Cama |
| 5,864,938 A | 2/1999 | Gansel et al. |
| 5,865,168 A | 2/1999 | Isaza |
| 5,865,171 A | 2/1999 | Cinquin |
| 5,865,174 A | 2/1999 | Kloeppel |
| 5,875,777 A | 3/1999 | Eriksson |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,899,203 A | 5/1999 | Defares et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,924,418 A | 7/1999 | Lewis |
| 5,927,274 A | 7/1999 | Servidio et al. |
| 5,931,160 A * | 8/1999 | Gilmore et al. .......... 128/204.21 |
| 5,932,812 A | 8/1999 | Delsing |
| 5,934,274 A | 8/1999 | Merrick et al. |
| 5,937,854 A | 8/1999 | Stenzler |
| 5,956,501 A | 9/1999 | Brown |
| 5,957,861 A | 9/1999 | Combs et al. |
| 5,957,885 A | 9/1999 | Bollish et al. |
| 5,971,937 A | 10/1999 | Ekstrom |
| 5,975,081 A | 11/1999 | Hood et al. |
| 5,979,440 A | 11/1999 | Honkonen et al. |
| 5,980,466 A | 11/1999 | Thomson |
| 6,012,034 A | 1/2000 | Hamparian et al. |
| 6,012,450 A | 1/2000 | Rubsamen |
| 6,017,315 A | 1/2000 | Starr et al. |
| 6,024,089 A | 2/2000 | Wallace et al. |
| 6,026,323 A | 2/2000 | Skladnev et al. |
| 6,032,119 A | 2/2000 | Brown et al. |
| 6,041,780 A | 3/2000 | Richard et al. |
| 6,047,860 A | 4/2000 | Sanders |
| 6,055,506 A | 4/2000 | Frasca, Jr. |
| 6,073,110 A | 6/2000 | Rhodes et al. |
| 6,076,523 A | 6/2000 | Jones et al. |
| 6,099,481 A | 8/2000 | Daniels et al. |
| 6,106,481 A | 8/2000 | Cohen |
| 6,113,552 A | 9/2000 | Shimazu et al. |
| 6,116,240 A | 9/2000 | Merrick et al. |
| 6,116,464 A | 9/2000 | Sanders |
| 6,118,847 A | 9/2000 | Hernandez-Guerra et al. |
| 6,119,684 A | 9/2000 | Nohl et al. |
| 6,123,073 A | 9/2000 | Schlawin et al. |
| 6,135,106 A | 10/2000 | Dirks et al. |
| 6,142,150 A | 11/2000 | O'Mahoney et al. |
| 6,148,814 A | 11/2000 | Clemmer et al. |
| 6,148,815 A | 11/2000 | Wolf |
| 6,155,257 A | 12/2000 | Lurie et al. |
| 6,158,432 A | 12/2000 | Biondi et al. |
| 6,159,147 A | 12/2000 | Lichter et al. |
| 6,161,539 A | 12/2000 | Winter |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,955 B1 | 4/2001 | Karakasoglu et al. |
| 6,220,245 B1 | 4/2001 | Takabayashi et al. |
| 6,223,744 B1 | 5/2001 | Garon |
| 6,224,553 B1 | 5/2001 | Nevo |
| 6,233,539 B1 | 5/2001 | Brown |
| 6,234,963 B1 | 5/2001 | Blike et al. |
| 6,240,920 B1 | 6/2001 | Strom |
| 6,251,082 B1 | 6/2001 | Rayburn |
| 6,261,238 B1 | 7/2001 | Gavriely |
| 6,269,810 B1 | 8/2001 | Brooker et al. |
| 6,269,812 B1 | 8/2001 | Wallace et al. |
| 6,273,088 B1 | 8/2001 | Hillsman |
| 6,273,444 B1 | 8/2001 | Power |
| 6,279,574 B1 | 8/2001 | Richardson et al. |
| 6,283,119 B1 | 9/2001 | Bourdon |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,372 B1 | 10/2001 | Servidio |
| 6,305,373 B1 | 10/2001 | Wallace et al. |
| 6,321,748 B1 | 11/2001 | O'Mahony |
| 6,322,502 B1 | 11/2001 | Schoenberg et al. |
| 6,325,785 B1 | 12/2001 | Babkes et al. |
| 6,339,410 B1 | 1/2002 | Milner et al. |
| 6,340,348 B1 | 1/2002 | Krishnan et al. |
| 6,342,040 B1 | 1/2002 | Starr et al. |
| 6,349,722 B1 | 2/2002 | Gradon et al. |
| 6,349,724 B1 | 2/2002 | Burton et al. |

(56) References Cited

U.S. PATENT DOCUMENTS

| | | |
|---|---|---|
| 6,355,002 B1 | 3/2002 | Faram et al. |
| 6,357,438 B1 | 3/2002 | Hansen |
| 6,360,745 B1 | 3/2002 | Wallace et al. |
| 6,362,620 B1 | 3/2002 | Debbins et al. |
| 6,367,475 B1 | 4/2002 | Kofoed et al. |
| 6,369,838 B1 | 4/2002 | Wallace et al. |
| 6,370,419 B1 | 4/2002 | Lampotang et al. |
| 6,377,046 B1 | 4/2002 | Debbins et al. |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,402,698 B1 | 6/2002 | Mault |
| 6,408,043 B1 | 6/2002 | Hu et al. |
| 6,412,483 B1 | 7/2002 | Jones et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |
| 6,439,229 B1 | 8/2002 | Du et al. |
| 6,450,164 B1 | 9/2002 | Banner et al. |
| 6,454,708 B1 | 9/2002 | Ferguson et al. |
| 6,459,933 B1 | 10/2002 | Lurie et al. |
| 6,463,930 B2 | 10/2002 | Biondi et al. |
| 6,467,478 B1 | 10/2002 | Merrick et al. |
| 6,471,658 B1 | 10/2002 | Daniels et al. |
| 6,488,029 B1 | 12/2002 | Hood et al. |
| 6,488,629 B1 | 12/2002 | Saetre et al. |
| RE37,970 E | 1/2003 | Costello, Jr. |
| 6,511,426 B1 | 1/2003 | Hossack et al. |
| 6,512,938 B2 | 1/2003 | Claure et al. |
| 6,515,683 B1 | 2/2003 | Wright |
| 6,517,497 B2 | 2/2003 | Rymut et al. |
| 6,533,723 B1 | 3/2003 | Lockery et al. |
| 6,533,730 B2 | 3/2003 | Strom |
| 6,543,449 B1 | 4/2003 | Woodring et al. |
| 6,543,701 B1 | 4/2003 | Ho |
| 6,544,192 B2 | 4/2003 | Starr et al. |
| 6,546,930 B1 | 4/2003 | Emerson et al. |
| 6,547,728 B1 | 4/2003 | Cornuejols |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,566,875 B1 | 5/2003 | Hasson et al. |
| 6,571,122 B2 | 5/2003 | Schroeppel et al. |
| 6,571,795 B2 | 6/2003 | Bourdon |
| 6,571,796 B2 | 6/2003 | Banner et al. |
| 6,578,575 B1 | 6/2003 | Jonson |
| 6,581,592 B1 | 6/2003 | Bathe et al. |
| 6,584,973 B1 | 7/2003 | Biondi et al. |
| 6,597,939 B1 | 7/2003 | Lampotang et al. |
| 6,599,252 B2 | 7/2003 | Starr |
| 6,603,494 B1 | 8/2003 | Banks et al. |
| 6,606,993 B1 | 8/2003 | Wiesmann et al. |
| 6,620,106 B2 | 9/2003 | Mault |
| 6,621,917 B1 | 9/2003 | Vilser |
| 6,622,726 B1 | 9/2003 | Du |
| 6,629,934 B2 | 10/2003 | Mault et al. |
| 6,630,176 B2 | 10/2003 | Li et al. |
| 6,644,310 B1 | 11/2003 | Delache et al. |
| 6,644,312 B2 | 11/2003 | Berthon-Jones et al. |
| 6,645,158 B2 | 11/2003 | Mault |
| 6,650,346 B1 | 11/2003 | Jaeger et al. |
| 6,651,653 B1 | 11/2003 | Honkonen et al. |
| 6,656,129 B2 | 12/2003 | Niles et al. |
| 6,668,824 B1 | 12/2003 | Isaza et al. |
| 6,668,829 B2 | 12/2003 | Biondi et al. |
| 6,671,529 B2 | 12/2003 | Claure et al. |
| 6,673,018 B2 | 1/2004 | Friedman |
| 6,675,801 B2 | 1/2004 | Wallace et al. |
| 6,679,258 B1 | 1/2004 | Strom |
| 6,681,764 B1 | 1/2004 | Honkonen et al. |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,974 B1 | 4/2004 | Moberg |
| 6,718,975 B2 | 4/2004 | Blomberg |
| 6,725,077 B1 | 4/2004 | Balloni et al. |
| 6,725,447 B1 | 4/2004 | Gilman et al. |
| 6,725,860 B2 | 4/2004 | Wallroth et al. |
| 6,733,449 B1 | 5/2004 | Krishnamurthy et al. |
| 6,738,079 B1 | 5/2004 | Kellerman et al. |
| 6,739,337 B2 | 5/2004 | Isaza |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,755,193 B2 | 6/2004 | Berthon-Jones et al. |
| 6,755,787 B2 | 6/2004 | Hossack et al. |
| 6,760,610 B2 | 7/2004 | Tschupp et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg et al. |
| 6,790,178 B1 | 9/2004 | Mault et al. |
| 6,792,066 B1 | 9/2004 | Harder et al. |
| 6,796,305 B1 | 9/2004 | Banner et al. |
| 6,801,227 B2 | 10/2004 | Bocionek et al. |
| 6,801,802 B2 | 10/2004 | Sitzman et al. |
| 6,805,118 B2 | 10/2004 | Brooker et al. |
| 6,807,965 B1 | 10/2004 | Hickle |
| 6,814,074 B1 | 11/2004 | Nadjafizadeh et al. |
| 6,820,614 B2 | 11/2004 | Bonutti |
| 6,820,618 B2 | 11/2004 | Banner et al. |
| 6,822,223 B2 | 11/2004 | Davis |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,242 B2 | 1/2005 | Younes |
| 6,839,753 B2 | 1/2005 | Biondi et al. |
| 6,845,773 B2 | 1/2005 | Berthon-Jones et al. |
| 6,858,006 B2 | 2/2005 | MacCarter et al. |
| 6,860,266 B2 | 3/2005 | Blike |
| 6,866,040 B1 | 3/2005 | Bourdon |
| 6,866,629 B2 | 3/2005 | Bardy |
| 6,893,397 B2 | 5/2005 | Bardy |
| 6,899,103 B1 | 5/2005 | Hood et al. |
| 6,899,683 B2 | 5/2005 | Mault et al. |
| 6,899,684 B2 | 5/2005 | Mault et al. |
| 6,910,481 B2 | 6/2005 | Kimmel et al. |
| 6,921,369 B2 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry et al. |
| 6,947,780 B2 | 9/2005 | Scharf |
| 6,951,541 B2 | 10/2005 | Desmarais |
| 6,954,702 B2 | 10/2005 | Pierry et al. |
| 6,956,572 B2 | 10/2005 | Zaleski |
| 6,960,854 B2 | 11/2005 | Nadjafizadeh et al. |
| 6,970,919 B1 | 11/2005 | Doi et al. |
| 6,976,958 B2 | 12/2005 | Quy |
| 6,986,347 B2 | 1/2006 | Hickle |
| 6,997,185 B2 | 2/2006 | Han et al. |
| 6,997,880 B2 | 2/2006 | Carlebach et al. |
| 7,008,380 B1 | 3/2006 | Rees et al. |
| 7,017,574 B2 | 3/2006 | Biondi et al. |
| 7,019,652 B2 | 3/2006 | Richardson |
| 7,033,323 B2 | 4/2006 | Botbol et al. |
| 7,036,504 B2 | 5/2006 | Wallace et al. |
| 7,039,878 B2 | 5/2006 | Auer et al. |
| 7,040,315 B1 | 5/2006 | Strömberg |
| 7,040,318 B2 | 5/2006 | Däscher et al. |
| 7,040,321 B2 | 5/2006 | Göbel |
| 7,046,254 B2 | 5/2006 | Brown et al. |
| 7,047,092 B2 | 5/2006 | Wimsatt |
| 7,051,736 B2 | 5/2006 | Banner et al. |

(56) References Cited

U.S. PATENT DOCUMENTS

| | | |
|---|---|---|
| 7,062,251 B2 | 6/2006 | Birkett et al. |
| 7,066,173 B2 | 6/2006 | Banner et al. |
| 7,077,125 B2 | 7/2006 | Scheuch |
| 7,077,131 B2 | 7/2006 | Hansen |
| 7,081,091 B2 | 7/2006 | Merrett et al. |
| 7,081,095 B2 | 7/2006 | Lynn et al. |
| RE39,225 E | 8/2006 | Isaza et al. |
| 7,083,574 B2 | 8/2006 | Kline |
| 7,089,927 B2 | 8/2006 | John et al. |
| 7,089,937 B2 | 8/2006 | Berthon-Jones et al. |
| 7,094,208 B2 | 8/2006 | Williams et al. |
| 7,116,810 B2 | 10/2006 | Miller et al. |
| 7,117,438 B2 | 10/2006 | Wallace et al. |
| 7,128,578 B2 | 10/2006 | Lampotang et al. |
| 7,147,600 B2 | 12/2006 | Bardy |
| 7,156,808 B2 | 1/2007 | Quy |
| 7,162,296 B2 | 1/2007 | Leonhardt et al. |
| 7,164,972 B2 | 1/2007 | Imhof et al. |
| 7,165,221 B2 | 1/2007 | Monteleone et al. |
| 7,169,112 B2 | 1/2007 | Caldwell |
| 7,172,557 B1 | 2/2007 | Parker |
| 7,182,083 B2 | 2/2007 | Yanof et al. |
| 7,187,790 B2 | 3/2007 | Sabol et al. |
| 7,188,621 B2 | 3/2007 | DeVries et al. |
| 7,201,734 B2 | 4/2007 | Hickle |
| 7,203,353 B2 | 4/2007 | Klotz et al. |
| 7,210,478 B2 | 5/2007 | Banner et al. |
| 7,211,049 B2 | 5/2007 | Bradley et al. |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,261,690 B2 | 8/2007 | Teller et al. |
| 7,264,730 B2 | 9/2007 | Connell et al. |
| 7,270,126 B2 | 9/2007 | Wallace et al. |
| 7,275,540 B2 | 10/2007 | Bolam et al. |
| 7,278,579 B2 | 10/2007 | Loffredo et al. |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,343,916 B2 | 3/2008 | Biondo et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,460,959 B2 | 12/2008 | Jafari |
| 7,464,339 B2 | 12/2008 | Keenan, Jr. et al. |
| 7,469,698 B1 | 12/2008 | Childers et al. |
| 7,487,773 B2 | 2/2009 | Li |
| 7,487,774 B2 | 2/2009 | Acker |
| 7,490,085 B2 | 2/2009 | Walker et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |

(56) References Cited

U.S. PATENT DOCUMENTS

| | | |
|---|---|---|
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0056358 A1 | 12/2001 | Dulong et al. |
| 2002/0026941 A1 | 3/2002 | Biondi et al. |
| 2002/0044059 A1 | 4/2002 | Reeder et al. |
| 2002/0077863 A1 | 6/2002 | Rutledge et al. |
| 2002/0091548 A1 | 7/2002 | Auer et al. |
| 2002/0177758 A1 | 11/2002 | Schoenberg et al. |
| 2002/0185127 A1* | 12/2002 | Melker et al. ............ 128/202.22 |
| 2003/0060723 A1 | 3/2003 | Joo et al. |
| 2003/0062045 A1 | 4/2003 | Woodring et al. |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko et al. |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0034289 A1 | 2/2004 | Teller et al. |
| 2004/0059604 A1 | 3/2004 | Zaleski |
| 2004/0073453 A1 | 4/2004 | Nenov et al. |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson et al. |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning et al. |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager et al. |
| 2005/0085869 A1 | 4/2005 | Tehrani et al. |
| 2005/0104860 A1 | 5/2005 | McCreary |
| 2005/0108057 A1 | 5/2005 | Cohen et al. |
| 2005/0112013 A1 | 5/2005 | DeVries et al. |
| 2005/0112325 A1 | 5/2005 | Hickle |
| 2005/0124866 A1 | 6/2005 | Elaz et al. |
| 2005/0133027 A1 | 6/2005 | Elaz et al. |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz et al. |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi et al. |
| 2005/0192488 A1 | 9/2005 | Bryenton et al. |
| 2005/0204310 A1 | 9/2005 | De Zwart et al. |
| 2005/0215904 A1 | 9/2005 | Sumanaweera et al. |
| 2005/0217674 A1 | 10/2005 | Burton et al. |
| 2005/0251040 A1 | 11/2005 | Relkuntwar et al. |
| 2005/0288571 A1 | 12/2005 | Perkins et al. |
| 2006/0047202 A1 | 3/2006 | Elliott |
| 2006/0078867 A1 | 4/2006 | Penny et al. |
| 2006/0080140 A1 | 4/2006 | Buttner et al. |
| 2006/0080343 A1 | 4/2006 | Carter et al. |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries et al. |
| 2006/0149144 A1 | 7/2006 | Lynn et al. |
| 2006/0149589 A1 | 7/2006 | Wager |
| 2006/0150982 A1 | 7/2006 | Wood |
| 2006/0155183 A1 | 7/2006 | Kroecker |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |

(56) References Cited

U.S. PATENT DOCUMENTS

| | | |
|---|---|---|
| 2006/0196507 A1 | 9/2006 | Bradley |
| 2006/0200009 A1 | 9/2006 | Wekell et al. |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017515 A1 | 1/2007 | Wallace et al. |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu et al. |
| 2007/0077200 A1 | 4/2007 | Baker |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |
| 2007/0215155 A1 | 9/2007 | Marx et al. |
| 2007/0225574 A1 | 9/2007 | Ueda |
| 2007/0227537 A1 | 10/2007 | Bemister et al. |
| 2007/0229249 A1 | 10/2007 | McNeal |
| 2007/0241884 A1 | 10/2007 | Yamazaki et al. |
| 2007/0265510 A1 | 11/2007 | Bardy |
| 2007/0265877 A1 | 11/2007 | Rice et al. |
| 2007/0271122 A1 | 11/2007 | Zaleski |
| 2007/0272241 A1 | 11/2007 | Sanborn et al. |
| 2007/0272242 A1 | 11/2007 | Sanborn et al. |
| 2007/0273216 A1 | 11/2007 | Farbarik |
| 2007/0276439 A1 | 11/2007 | Miesel et al. |
| 2007/0284361 A1 | 12/2007 | Nadjafizadeh et al. |
| 2007/0293741 A1 | 12/2007 | Bardy |
| 2008/0000477 A1 | 1/2008 | Huster et al. |
| 2008/0000479 A1 | 1/2008 | Elaz et al. |
| 2008/0007396 A1 | 1/2008 | Parkulo |
| 2008/0021379 A1 | 1/2008 | Hickle |
| 2008/0033661 A1 | 2/2008 | Syroid et al. |
| 2008/0039735 A1 | 2/2008 | Hickerson |
| 2008/0041380 A1 | 2/2008 | Wallace et al. |
| 2008/0045844 A1 | 2/2008 | Arbel et al. |
| 2008/0047554 A1 | 2/2008 | Roy et al. |
| 2008/0053438 A1 | 3/2008 | DeVries et al. |
| 2008/0053441 A1 | 3/2008 | Gottlib et al. |
| 2008/0064963 A1 | 3/2008 | Schwaibold et al. |
| 2008/0065420 A1 | 3/2008 | Tirinato et al. |
| 2008/0066753 A1 | 3/2008 | Martin et al. |
| 2008/0072896 A1 | 3/2008 | Setzer et al. |
| 2008/0072900 A1 | 3/2008 | Kenyon et al. |
| 2008/0072901 A1 | 3/2008 | Habashi |
| 2008/0072902 A1 | 3/2008 | Setzer et al. |
| 2008/0076970 A1 | 3/2008 | Foulis et al. |
| 2008/0077033 A1 | 3/2008 | Figueiredo |
| 2008/0077038 A1 | 3/2008 | McDonough et al. |
| 2008/0077436 A1 | 3/2008 | Muradia |
| 2008/0078390 A1 | 4/2008 | Milne et al. |
| 2008/0083644 A1 | 4/2008 | Janbakhsh et al. |
| 2008/0091122 A1 | 4/2008 | Dunlop |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz et al. |
| 2008/0125873 A1 | 5/2008 | Payne et al. |
| 2008/0161653 A1 | 7/2008 | Lin et al. |
| 2008/0172249 A1 | 7/2008 | Glaser-Seidnitzer |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0185009 A1 | 8/2008 | Choncholas et al. |
| 2008/0205427 A1 | 8/2008 | Jost et al. |
| 2008/0208012 A1 | 8/2008 | Ali |
| 2008/0214947 A1 | 9/2008 | Hunt et al. |
| 2008/0230057 A1 | 9/2008 | Sutherland |
| 2008/0236582 A1 | 10/2008 | Tehrani |
| 2008/0236585 A1 | 10/2008 | Parker et al. |
| 2008/0243016 A1 | 10/2008 | Liao et al. |
| 2008/0251070 A1 | 10/2008 | Pinskiy et al. |
| 2008/0255880 A1 | 10/2008 | Beller et al. |
| 2008/0258929 A1 | 10/2008 | Maschke |
| 2008/0270912 A1 | 10/2008 | Booth |
| 2008/0281219 A1 | 11/2008 | Glickman et al. |
| 2008/0293025 A1 | 11/2008 | Zamierowsi et al. |
| 2008/0295830 A1 | 12/2008 | Martonen et al. |
| 2008/0295839 A1 | 12/2008 | Habashi |
| 2008/0306351 A1 | 12/2008 | Izumi |
| 2008/0308109 A1 | 12/2008 | Brain |
| 2008/0312594 A1 | 12/2008 | Ullrich |
| 2008/0312954 A1 | 12/2008 | Ullrich et al. |
| 2008/0319513 A1 | 12/2008 | Pu et al. |
| 2009/0005651 A1 | 1/2009 | Ward et al. |
| 2009/0007909 A1 | 1/2009 | Carrico |
| 2009/0038921 A1 | 2/2009 | Kaps et al. |
| 2009/0054743 A1 | 2/2009 | Stewart |
| 2009/0055735 A1 | 2/2009 | Zaleski |
| 2009/0062725 A1 | 3/2009 | Goebel |
| 2009/0063181 A1 | 3/2009 | Nho et al. |
| 2009/0065004 A1 | 3/2009 | Childers et al. |
| 2009/0076342 A1 | 3/2009 | Amurthur et al. |
| 2009/0124917 A1 | 5/2009 | Hatlestad et al. |
| 2009/0125333 A1 | 5/2009 | Heywood et al. |
| 2009/0126734 A1 | 5/2009 | Dunsmore et al. |
| 2009/0131758 A1 | 5/2009 | Heywood et al. |
| 2009/0133701 A1 | 5/2009 | Brain |
| 2009/0143694 A1 | 6/2009 | Krauss et al. |
| 2009/0145438 A1 | 6/2009 | Brain |
| 2009/0149200 A1 | 6/2009 | Jayasinghe et al. |
| 2009/0149723 A1 | 6/2009 | Krauss et al. |
| 2009/0149927 A1 | 6/2009 | Kneuer et al. |
| 2009/0150184 A1 | 6/2009 | Spahn |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0192421 A1 | 7/2009 | Huster et al. |
| 2009/0205661 A1 | 8/2009 | Stephenson et al. |
| 2009/0205663 A1 | 8/2009 | Vandine et al. |
| 2009/0209828 A1 | 8/2009 | Musin |
| 2009/0209849 A1 | 8/2009 | Rowe et al. |
| 2009/0216145 A1 | 8/2009 | Skerl et al. |
| 2009/0221926 A1 | 9/2009 | Younes |
| 2009/0240523 A1 | 9/2009 | Friedlander et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247891 A1 | 10/2009 | Wood |
| 2009/0250054 A1 | 10/2009 | Loncar et al. |
| 2009/0301486 A1 | 12/2009 | Masic |
| 2009/0301487 A1 | 12/2009 | Masic |
| 2009/0301490 A1 | 12/2009 | Masic |

(56) References Cited

U.S. PATENT DOCUMENTS

| | | |
|---|---|---|
| 2009/0301491 A1 | 12/2009 | Masic et al. |
| 2010/0004517 A1 | 1/2010 | Bryenton et al. |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |
| 2010/0063350 A1 | 3/2010 | Henke et al. |
| 2010/0063365 A1 | 3/2010 | Pisani et al. |
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | van der Zande et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0095961 A1 | 4/2010 | Tornesel et al. |
| 2010/0130873 A1 | 5/2010 | Yuen et al. |
| 2010/0139660 A1 | 6/2010 | Adahan |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0274100 A1 | 10/2010 | Behar et al. |
| 2010/0282259 A1 | 11/2010 | Figueiredo et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2011/0004489 A1 | 1/2011 | Schoenberg et al. |
| 2011/0009746 A1 | 1/2011 | Tran et al. |
| 2011/0011400 A1 | 1/2011 | Gentner et al. |
| 2011/0015493 A1 | 1/2011 | Koschek |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0054289 A1 | 3/2011 | Derchak et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |

(56) References Cited

U.S. PATENT DOCUMENTS

FOREIGN PATENT DOCUMENTS

| | | |
|---|---|---|
| EP | 1421966 | 5/2004 |
| EP | 1464357 | 10/2004 |
| FR | 2729084 | 7/1996 |
| GB | 2319967 | 6/1998 |
| NL | 8801322 | 12/1989 |
| WO | WO9014852 A1 | 12/1990 |
| WO | WO9308534 A1 | 4/1993 |
| WO | WO9312823 A2 | 7/1993 |
| WO | WO9314696 A1 | 8/1993 |
| WO | WO9414374 A1 | 7/1994 |
| WO | WO9508471 A1 | 3/1995 |
| WO | WO9532480 A1 | 11/1995 |
| WO | WO9624285 A1 | 8/1996 |
| WO | WO9720592 A1 | 6/1997 |
| WO | WO9811840 A1 | 3/1998 |
| WO | WO9814116 A2 | 4/1998 |
| WO | WO9829790 A2 | 7/1998 |
| WO | WO9833554 A1 | 8/1998 |
| WO | WO9840014 A1 | 9/1998 |
| WO | WO9841267 A1 | 9/1998 |
| WO | WO9841267 C1 | 9/1998 |
| WO | WO9841269 A1 | 9/1998 |
| WO | WO9841270 A1 | 9/1998 |
| WO | WO9841271 A1 | 9/1998 |
| WO | WO9858219 A1 | 12/1998 |
| WO | WO9903524 A1 | 1/1999 |
| WO | WO9952431 A1 | 10/1999 |
| WO | WO9952437 A1 | 10/1999 |
| WO | WO9959460 A2 | 11/1999 |
| WO | WO9962403 A1 | 12/1999 |
| WO | WO0018293 | 4/2000 |
| WO | WO0019886 A1 | 4/2000 |
| WO | WO0062664 A1 | 10/2000 |
| WO | WO0100264 A1 | 1/2001 |
| WO | WO0100265 A1 | 1/2001 |
| WO | WO0128416 A1 | 4/2001 |
| WO | WO0134022 A1 | 5/2001 |
| WO | WO0245566 A2 | 6/2002 |
| WO | WO02082967 A2 | 10/2002 |
| WO | WO03015005 A2 | 2/2003 |
| WO | WO03024317 A2 | 3/2003 |
| WO | WO03045493 A2 | 6/2003 |
| WO | WO03053503 A1 | 7/2003 |
| WO | WO03060650 A2 | 7/2003 |
| WO | WO03060651 A2 | 7/2003 |
| WO | WO03075989 A2 | 9/2003 |
| WO | WO03075990 A2 | 9/2003 |
| WO | WO03075991 A1 | 9/2003 |
| WO | WO03084405 A2 | 10/2003 |
| WO | WO2004014216 A2 | 2/2004 |
| WO | WO2004014226 A1 | 2/2004 |
| WO | WO2004032719 A2 | 4/2004 |
| WO | WO2004043254 A1 | 5/2004 |
| WO | WO2005010796 | 2/2005 |
| WO | WO2005024729 A1 | 3/2005 |
| WO | WO2005055825 A1 | 6/2005 |
| WO | WO2005056087 A1 | 6/2005 |
| WO | WO2005069740 A2 | 8/2005 |
| WO | WO2005077260 A1 | 8/2005 |
| WO | WO2005112739 A1 | 12/2005 |
| WO | WO2006008745 A2 | 1/2006 |
| WO | WO2006009830 A2 | 1/2006 |
| WO | WO2006037184 A1 | 4/2006 |
| WO | WO2006050388 A2 | 5/2006 |
| WO | WO2006051466 A1 | 5/2006 |
| WO | WO2006078432 A2 | 7/2006 |
| WO | WO2006094055 A2 | 9/2006 |
| WO | WO2006096080 A1 | 9/2006 |
| WO | WO2006109072 A2 | 10/2006 |
| WO | WO2006123956 A1 | 11/2006 |
| WO | WO2006125986 A1 | 11/2006 |
| WO | WO2006125987 A1 | 11/2006 |
| WO | WO2006125989 A1 | 11/2006 |
| WO | WO2006125990 A1 | 11/2006 |
| WO | WO2006137067 A2 | 12/2006 |
| WO | WO2007033050 A2 | 3/2007 |
| WO | WO2007106804 A2 | 9/2007 |
| WO | WO 2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual Ventilator System, Nellcor Puritan Bennett, Part No. 4-075609-00, Rev. G, Oct. 2006, pp. 1-424.

Drager—Evita Intensive Care Ventilator Instruction Manual.

Marketing Brochure—Pediatric—Adult Star 1500 Ventilator—Infrasonics, Inc., Star Products, 1996.

Ohmeda Modulus CD Anesthesia System Operation and Maintenance, Jun. 1994.

U.S. Appl. No. 13/163,531, Office Action mailed Feb. 20, 2013, 8 pgs.

U.S. Appl. No. 13/163,531, Notice of Allowance mailed Jun. 10, 2013, 11 pgs.

* cited by examiner

VENTILATOR BREATH DISPLAY AND GRAPHIC USER INTERFACE

CROSS REFERENCE TO RELATED APPLICATIONS

This application is a continuation of U.S. patent application Ser. No. 13/163,531 filed Jun. 17, 2011; which is a continuation of U.S. patent application Ser. No. 11/856,632 filed Sep. 17, 2007, now U.S. Pat. No. 8,001,967; which is a continuation of U.S. application Ser. No. 11/366,259 filed Mar. 2, 2006, now U.S. Pat. No. 7,270,126; which is a continuation of U.S. patent application Ser. No. 10/733,794 filed Dec. 10, 2003, now U.S. Pat. No. 7,036,504; which is a continuation of U.S. patent application Ser. No. 09/882,200 filed Jun. 15, 2001, now U.S. Pat. No. 6,675,801; which is a continuation of U.S. patent application Ser. No. 09/253,387 filed Feb. 19, 1999, now U.S. Pat. No. 6,269,812; which is a continuation of U.S. patent application Ser. No. 08/818,807 filed Mar. 14, 1997, now U.S. Pat. No. 5,881,723, the contents of which are hereby incorporated in their entirety by reference.

BACKGROUND OF THE INVENTION

1. Field of the Invention

This invention relates generally to the field of medical equipment for respiratory therapy and more specifically to the user interface for a ventilator used for monitoring and controlling the breathing of a patient.

2. Description of the Related Art

Modern patient ventilators are designed to ventilate a patient's lungs with breathing gas, and to thereby assist a patient when the patient's ability to breathe on his own is somehow impaired. As research has continued in the field of respiration therapy, a wide range of ventilation strategies have been developed. For example, pressure assisted ventilation is a strategy often available in patient ventilators and includes the supply of pressure assistance when the patient has already begun an inspiratory effort. With such a strategy, it is desirable to immediately increase the pressure after a breath is initiated in order to reach a target airway pressure for the pressure assistance. This rise in pressure in the patient airway which supplies breathing gas to the patient's lungs allows the lungs to be filled with less work of breathing by the patent. Conventional pressure assisted ventilator systems typically implement a gas flow control strategy of stabilizing pressure support after a target pressure is reached to limit patient airway pressure. Such a strategy also can include programmed reductions in the patient airway pressure after set periods of the respiratory cycle in order to prepare for initiation of the next patient breath.

As patient ventilator systems and their various components, including sensors and control systems, have become more sophisticated, and more understanding is gained about the physiology of breathing and the infirmities and damage which form the requirements for respiratory therapy, the number of variables to be controlled and the timing and interrelationships between the parameters have begun to confront the caregiver with a daunting number of alternative therapeutic alternatives and ventilator settings. Also, in such a complex environment, the interface between the ventilator and the caregiver has often not been adaptable to the capabilities of the operator, thus running the chance of either limiting the choices available to a sophisticated user or allowing a relatively less sophisticated user to chose poorly from the alternatives presented. Thus, it would be beneficial if a ventilator interface guided the user through the setup or therapy modification process, illustrating the relationship between changes, preventing incorrect or dangerous settings and sounding alarms or other audible indications of invalid settings when something is about to done that exceeds limits, but also allowing the advanced and sophisticated user to gain access to the full range of ventilator capabilities through an interface which both presents the various parameters and allows the visualization of their relationships.

Clinical treatment of a ventilated patient often requires that the breathing characteristics of the patient be monitored to detect changes in the breathing patterns of the patient. Many modern ventilators allow the visualization of patient breathing patterns and ventilator function and the caregiver adjusts the settings of the ventilator to fine tune the respiratory strategy being performed to assist the patient's breathing. However, these systems have been, up until now, relatively difficult to use by the unsophisticated user unless a limited number of options are selected. For example, in one prior art system, only a single respiratory parameter may be altered at a time. Moreover, the various respiratory parameters must often be entered into the ventilator controller in a prescribed order, or, where no order is prescribed, certain orders of entry should be avoided, otherwise the intermediate state of the machine before entry of the remaining parameters may not be appropriate for the patient. This inflexible approach to ventilator setup requires additional time and training if the user is to quickly and efficiently use the ventilator in a critical care environment.

Previous systems have also been deficient in that it is often difficult to determine the underlying fault that has caused an alarms to be sounded, and what controls or settings should be adjusted to cure the problem causing the alarm. For example, prior alarm systems have consisted of nothing more than a blinking display or light with an alarm to alert the user that a problem existed. Similarly, many prior art systems provided only limited assistance to a user or technician in setting the parameters to be used during treatment. For example, if a technician attempted to enter a setting that was inappropriate for the patient because of body size or for some other reason, the only alarm provided may have been an auditory indication that the value was not permitted, but no useful information was provided to assist the technician in entering an appropriate setting.

One problem consistently presented by prior art ventilator control systems has been that the user interface has offered relatively little to guide and inform the user during the setup and use of the ventilator. Prior systems typically utilized a single visual display of the operating parameters of the ventilator and sensed patient parameters. Alternatively, prior systems may have numerous fixed numeric displays, certain of which may not be applicable during all ventilation therapies. Even when more than one display has been provided, users typically received limited feedback, if any, from the control system indicating the effect that changing one particular setting had on the overall respiratory strategy. If a parameter was to be adjusted, the display would change to display that particular parameter upon actuation of the appropriate controls, and allow entry of a value for that parameter. However, the user was provided with no visual cue as to how the change in the parameter value would effect the overall ventilation strategy, and thus had no assistance in determining whether the value entered for the parameter was appropriate for the patient.

What has been needed and heretofore unavailable in patient ventilators is a user friendly graphic interface that provides for simultaneous monitoring and adjustment of the various parameters comprising a respiratory strategy. Such an interface would also preferably guide sophisticated users in implementing ventilation therapies, provide guidance on the relationships between parameters as they are adjusted, allow rapid return to safe operation in the event that an undesirable strategy was inadvertently entered, provide alarms that are easily understood and corrected and present all of the relevant information in an easily understood and graphic interface. The present invention fulfills these and other needs.

SUMMARY OF THE INVENTION

Briefly, and in general terms, the present invention is directed to a graphic user interface system for controlling a computer controlled ventilator to provide respiratory therapy to a patient. In a broad aspect of the invention, the invention includes a digital processor, a touch sensitive display screen and entry means cooperating to provide a user-friendly graphic interface for use in setting up and carrying out a wide variety of respiratory therapies. The processor controls the displaying of a plurality of screens, including user selectable graphic on-screen buttons for setting the values of various ventilator operating parameters for controlling the ventilator. Depending on the on-screen button touched, the processor causes different graphics to be displayed on the screens, provides graphic representations of the effect on the overall respiratory strategy caused by changes to the settings, and may also provide displays of patient data, alarm conditions, and other information.

In one preferred embodiment of the invention, the system includes the use of a digitally encoded knob for altering selected and displayed values of ventilation parameters, with the acceptable values indicated and unacceptable values alarmed and/or limited to prevent harm to the patient. The digital encoded rotation of the knob may be analyzed by the processor and a magnification factor applied to the knob output to increase the speed with which displayed values are altered. The magnification factor may also be used in the event of an overshoot condition to assist a user in recovering from the overshoot.

In another preferred embodiment of the invention, the processor may detect the connection of a patient to the ventilator when the ventilator is powered-up. The processor may then, in response to such a detection, start up the ventilator using a predetermined set of ventilator control settings deemed to be safe for the widest possible variety of patients.

In a further preferred embodiment of the invention, the processor may only display ventilator control settings appropriate for a selected mode of ventilation. The ranges of values of the appropriate settings, or bounds of the ventilation, may be limited by the processor in response to the selected mode of ventilation such that only those values determined to be appropriate are displayed, thus limiting the opportunity to select incorrect settings. Additionally, the processor may be responsive to specific values entered for certain of the ventilator settings to adjust the ranges of values allowed for ventilator settings dependent on the certain settings. Further, the processor may be programmed to require that a so called "ideal body weight" be entered before beginning ventilation of a patient, and then only ranges of values for settings that would be appropriate for ventilation of a patient with that ideal body weight are displayed.

In another presently preferred embodiment of the invention, the graphic user interface system includes at least two touch sensitive screen displays, a plurality of manual parameter controls, including at least one control knob that is activated upon selection of a parameter to be controlled and displayed on the screen, and a microprocessor controller which controls the logic and arrangement of the screen displays and the interface with the ventilator. The system of the invention includes protocols programmed into the microprocessor for entry of parameters within ranges predetermined to be appropriate for the patient parameters entered, alarms and other audible indications of invalid entry associated with entries outside of the acceptable ranges of parameters or inappropriate operation such as startup with a patient connected to the ventilator, and the ability to lock selected parameters while allowing for user variation of other parameters.

In another presently preferred embodiment of the invention, the user is provided a graphic interface in which the user is allowed to view and adjust a variety of alarm limits and is able to vary the levels at which the alarms are set off, within limits that are preset by the programming of the microprocessor as representative of values that are not to be exceeded, either as a function of ideal body weight or general parameters for all patients. The resultant setting of a filtered set of alarms may then be used by the user to avoid the setting of parameters that are likely to result in patient distress or other problems with the therapy, while still allowing the sophisticated user to configure a therapy that is customized for the particular patient.

In one presently preferred embodiment, the invention also allows the user an "undo" option in which a previously successful setting is reestablished after the user realizes that a series of proposed changes are likely to unworkable for the patient.

In yet another presently preferred embodiment of the invention, the user is provided with alarm indicators indicating the severity of a particular alarm. Alarm messages are also displayed in a selected screen area of the graphic user interface to assist the user in alarm recognition and understanding. Each alarm message may comprise an identifying message identifying the alarm being indicated, an analysis message providing information about the condition that caused the alarm to be indicated, and a remedy message suggesting steps that may be taken by the user to correct the alarm condition.

In a further currently preferred embodiment of the invention, the processor allows the user to configure the graphic user interface to provide a display of the current and/or proposed breath parameters and a graphic representation of the breath timing controlled by those parameters. Such a display allows the visualization of relationships between breath parameters, and, while parameters are being changed, provides the user with a visual representation of the effect of the proposed changes on the ventilation strategy while simultaneously allowing the user to view current settings, thus allowing the user to simultaneously view "where they are now" and "where they are going to be."

From the above, it may be seen that the present invention represents a quantum leap forward in the user interface available for patient ventilation. While assisting the sophisticated user in both visualizing the ventilation strategy and performance of the patient on the ventilator, it also guides and controls the less sophisticated user in setup and understanding of the relationships between ventilator settings. The invention provides these benefits while enforcing fail-safe functioning in the event of a variety of inadvertent or erroneous settings or circumstances.

These and other features and advantages of the invention will become apparent from the following detailed description, taken in conjunction with the accompanying drawings, which illustrate, by way of example, the features of the invention.

BRIEF DESCRIPTION OF THE DRAWINGS

In the drawings, where like reference numerals indicate like or similar components, elements and features across the several figures.

DETAILED DESCRIPTION OF THE PREFERRED EMBODIMENTS

The present invention provides a sophisticated graphic user interface and ventilator breath display capability that allows great flexibility in the setup of the ventilator and visualization of the effect that proposed changes to the ventilator setup may have on the ventilation strategy. More particularly, the invention provides a graphic representation of a breath cycle that allows the user to visually evaluate the effect of such changes, and also to select among appropriate parameters a parameter to "lock" and hold constant while other parameters are changed.

The drawings will now be described in more detail, wherein like referenced numerals refer to like or corresponding elements among the several drawings.

Figure 1:
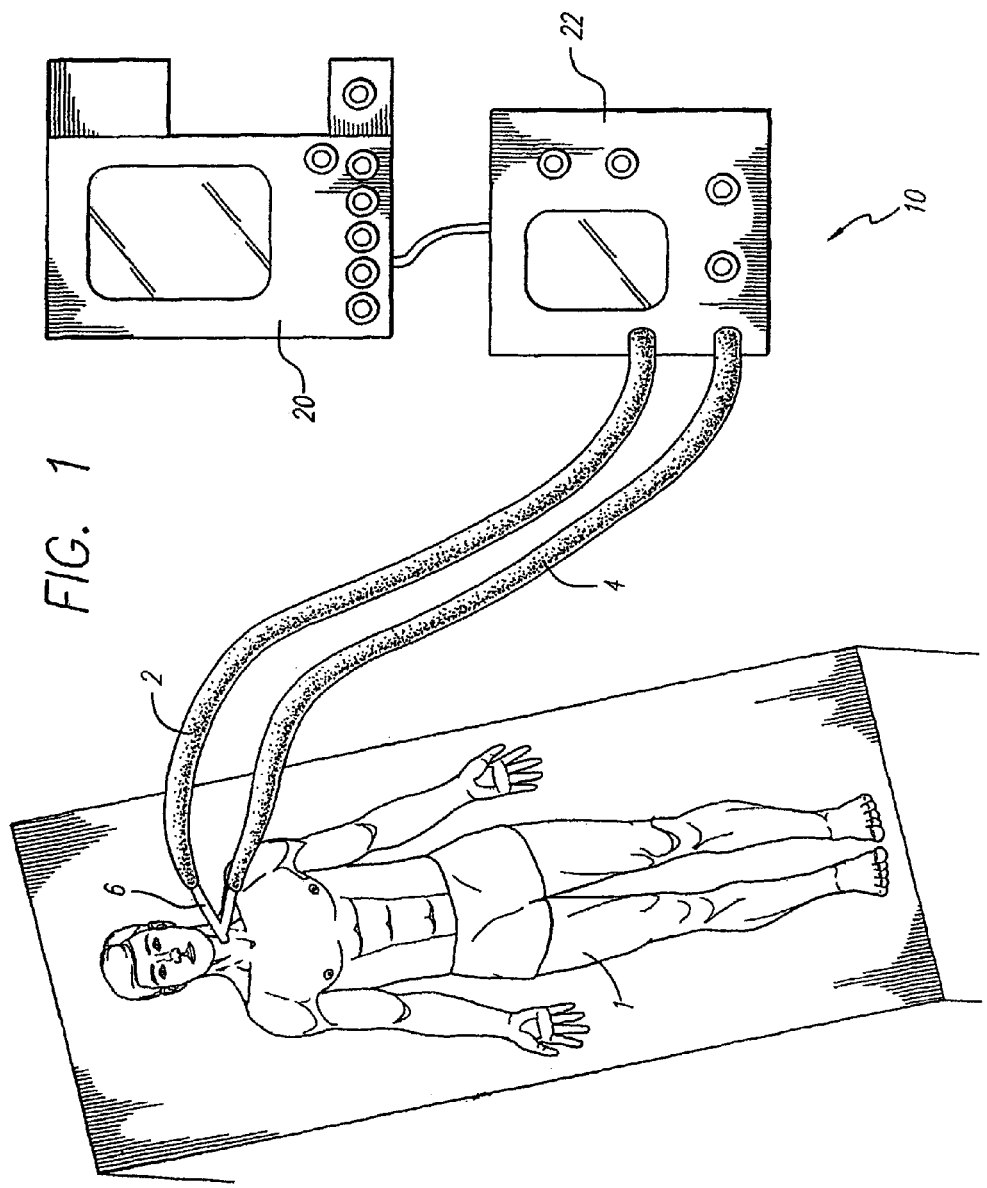
FIG. 1 is a schematic diagram of showing a patient receiving respiratory therapy from a ventilator system comprising a graphic user interface and a respirator constituting one embodiment of the present invention.

FIG. 1 shows a patient 1 receiving respiratory therapy from a ventilator system having a graphic user interface 20 connected to and controlling a breath delivery unit, or respirator 22. The patient is connected to the respirator 22 by a patient circuit comprising an inspiratory line 2, and expiratory line 4, and a patient connection tube 6, all connected by a patient connector (not shown) of a type well-known in the art. The respirator 22 includes a processor or controller 60 which controls the real-time operation of the respirator 22.

Figure 2:
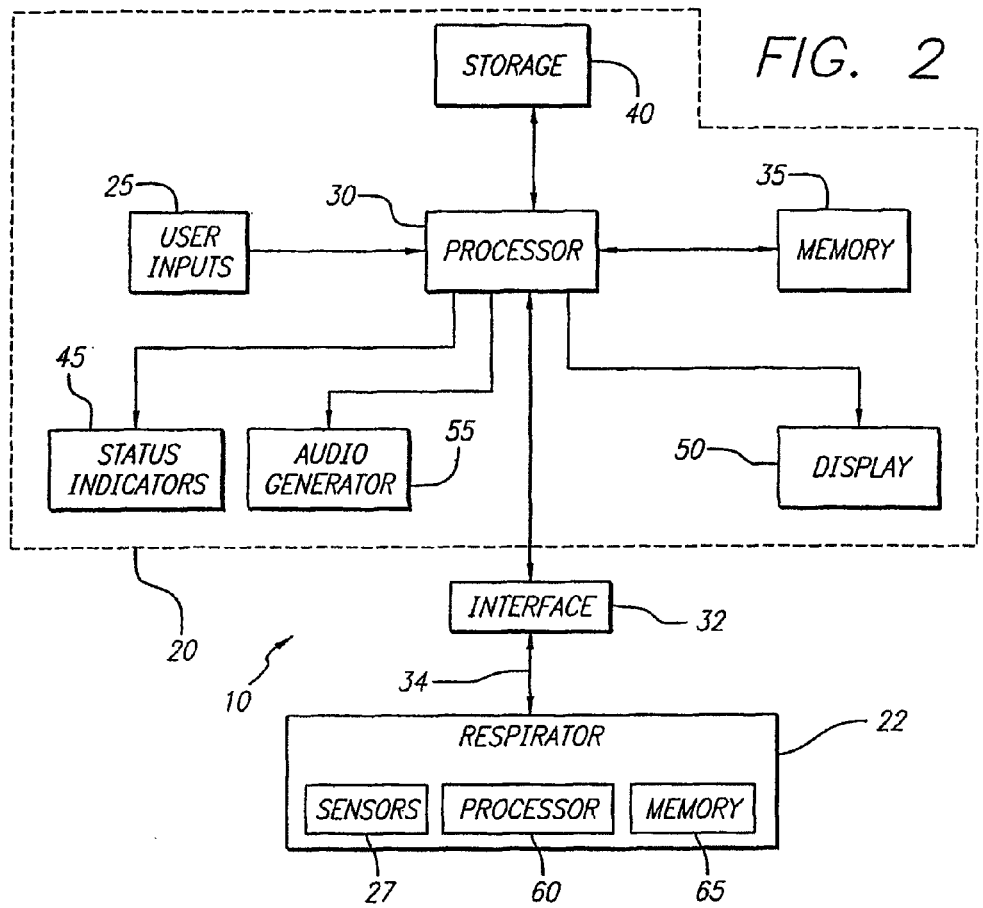
FIG. 2 is a schematic diagram, primarily in block form, of the various subsystems of the graphic user interface shown in FIG. 1.

FIG. 2 depicts the graphic user interface 20 of FIG. 1 in more detail. Generally, the graphic user interface 20 comprises user inputs 25, a processor 30 and memory 35 comprising read only memory, random access memory or both. The memory 30 may be used to store current settings, system status, patient data and ventilatory control software to be executed by the computer. The processor 30 may also be connected to a storage device, such as battery protected memory, a hard drive, a floppy drive, a magnetic tape drive or other storage media for storing patient data and associated ventilator operating parameters. The processor 30 accepts input received from the user inputs 25 to control the respirator 22. The ventilation control system 20 may also include status indicators 45, a display for displaying patient data and ventilator settings and an audio generator for providing audible indications of the status of the ventilator system 10.

The memory 35 and a memory 65 associated with the respirator processor 60 may be non-volatile random access memory (NVRAM) for storing important, persistent variables and configuration settings, such as current breath mode setup. Typically, during normal operation of the ventilation control system 20, such an NVRAM functions similarly to a typical random access memory. If, however, a low-voltage condition is detected, such as may occur during a brown-out or at the beginning of a power failure, the NVRAM automatically stores its data into non-volatile storage.

The graphic user interface 20 includes an interface 32 for providing control signals from the processor 30 to the respirator processor 60 of the respirator 22, and also for receiving signals from sensors 27 associated with the respirator 22 indicative of patient condition and the status of the respirator 22. The processor 30 of the graphic user interface 20 may also receive input representative of various clinical parameters indicating clinical condition of the patient 1 and the status of the respiratory therapy from the sensors 27 in the respirator 22. The interface may include, for example, an ethernet connection of a RS-232 serial interface. A cable 34 having an appropriate number of conductors is used to connect the respirator 22 to an appropriate connector (not shown) of the interface 32.

Figure 3:
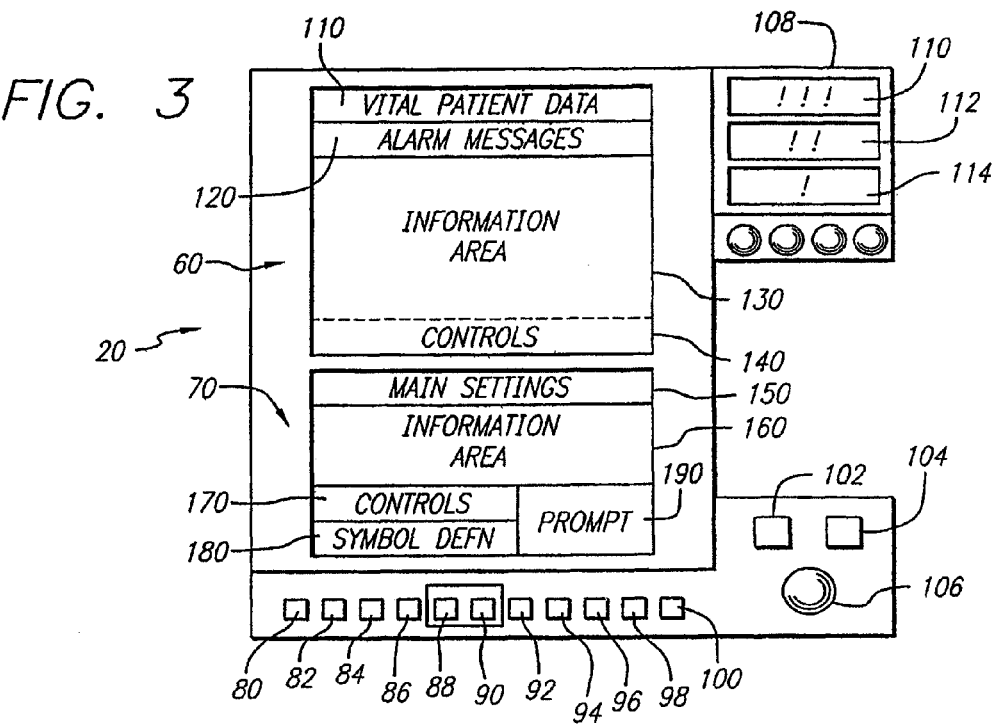
FIG. 3 is frontal plan view showing external details of graphic user interface of FIG. 1.

A preferred embodiment of the display 50 incorporating a user interface is illustrated in FIG. 3. Generally, the display 50 comprises an upper display 60 and a lower display 70, dedicated keys 80, 82, 84, 86, 88, 90, 92, 94, 96, 98, 100, 102, 104 and knob 106. As will be described in more detail below, additional user inputs are dynamically provided by on-screen buttons that are drawn on the upper and lower displays 60 and 70. Typically, each dedicated key or on-screen button includes, within the outline of the button, either a graphic icon or text identifying the purpose of the button to the user. These graphic icons or text enhance the ease of use of what would otherwise be a confusing array of user inputs. Moreover, the use of graphic icons or text to identify the function of dynamically generated on-screen buttons provides for virtually unlimited opportunities to add functions to the graphic user interface 20 by upgrading the programming of the processor 30 as new functions are desired by the users of the system. Additionally, the use of graphic icons overcomes the potential problem of identifying the functions of a button where language comprehension may be a problem, such as the use of the ventilator in a country where English is not readily understood.

Referring again to FIG. 3, key 80 is identified with a graphic design in the form of a stylized padlock. Actuation of key 80 by an operator locks the keys and buttons of the graphic user interface 20 to prevent inadvertent altering of the settings of the system. Keys 82 and 84 control the contrast and brightness of the displays 60, 70. Key 86 bears a stylized graphic design representative of a speaker emitting sound, and a graphic indicative of a volume control. Thus, key 86 is easily identifiable as a control for altering the loudness of audible alarm signals provided by the graphic user interface 20. Key 92 bears a "?" and actuation of key 92 activates a help system to assist a user in operating the graphic user interface 20.

Keys 94, 96, 98 and 100 control various aspects of the ventilator, and are used by an operator to override the automatic settings of the graphic user interface 20. When key 94 is pressed, the processor 30 of the graphic user interface 20 provides a signal over the 32 to the processor in the respirator 22 instructing the respirator processor to ventilate the patient with 100% oxygen for two minutes. The processor in the respirator 22 also starts a timer and causes the value of the time at any given instant to be written to a memory associated with the respirator processor. When the value in the respirator memory is equal to two (2) minutes, indicating that the 100% oxygen gas mixture has been provided to the patient for two (2) minutes, the respirator processor controls the respirator 22 to stop the flow of the 100% oxygen to the patient. If the user presses key 94 during the two (2) minute duration of the 100% oxygen ventilation, the value of the time stored in the memory is reset to "0" and timing continues for an additional two minutes. Typically, the respirator processor may be programmed to respond to any number of actuations of key 94 without prompting the user for validation or before sounding and displaying an alarm. Alternatively, the respirator processor may be programmed to respond to only a limited number of actuation of key 94 before sending a signal through the interface 32 to the processor 30 of the graphic user interface 20 requesting the processor 30 to provide a visual prompt on the display 50 and/or to control the audio generator 55 to sound an audible alarm indicating that an allowed number of actuations of key 94 has been exceeded.

When key 96 is pressed during an exhalation, the processor 30 controls the ventilator to immediately provide an inspiration. Actuation of key 98 results in an extension of the expiration phase. Similarly, actuation of key 100 results in a lengthening of the inspiration phase.

Key 102 is labeled with the text "Clear" and actuation of key 102 causes proposed changes to the value of a currently selected setting, to be discussed in more detail below, to be cleared. Key 104 is labeled with the text "Accept." When key 104 is touched, any proposed changes to the ventilator settings are confirmed, and become the current ventilator settings.

Knob 106 is used to adjust the value of an individual setting selected by pressing either keys 82, 84 and 86 or certain on-screen buttons. Knob 106 is mounted on a shaft whose rotation is digitally detected by a rotary encoder/decoder, such that the processor 30 receives signals indicating not only the magnitude of the rotation of knob 106, but also the speed and rate of acceleration and deceleration of the rotation of knob 106. These signals are interpreted by the processor 30 to display allowable values for the selected setting. In one embodiment of the present invention, the processor 30 is responsive to the signals indicative of the speed of rotation of knob 106 to calculate a velocity based magnification factor dependent on how fast and how long the user turned the knob that is applied by the processor 30 to adjust the increment of the values displayed. The processor 30 uses this magnifying factor to increment the displayed values in larger increments when knob 106 is rotated rapidly, and incrementing the displayed values in smaller increments when knob 106 is rotated slowly.

A common problem using rotating knobs where a magnification factor is applied in this manner is that there is inevitable "overshoot" of the desired value. Following an overshoot the user must reverse the direction of rotation of the knob. This reduces the speed of rotation of the knob to zero, and eliminates the magnification. Elimination of the magnification, however, results in more rotation and time to recover from the overshoot. One novel aspect of the present invention is that the processor 30 does not reduce the magnification factor to zero when the knob is counter rotated, as described above. Rather, the processor 30 applies a magnification factor to the counter rotation to reduce the amount of rotation of the knob 106 necessary to recover from the overshoot. The processor sets a time-based limit on how quickly the magnification factor is allowed to decrease, thus ensuring that some magnification remains during overshoot recovery.

Additionally, the processor 30 may provide signals to the audio generator 55 to cause the audio generator 55 to provide an audible indication of the rotation of knob 106. For example, the audio generator 55 may generate a "click" for a predetermined amount of rotation of the knob 106 or to signify that an on-screen button or dedicated key has been actuated. The audio generator 55 may also provide an audio signal to the user if the maximum or minimum value of the range of values for the selected setting has been reached, indicating that further rotation of the knob 106 will not cause any larger or smaller values to be displayed.

Referring again to FIG. 3, the display area of the ventilation control system 20 comprises an upper display 60 and a lower display 70. The upper display 60 is divided into four non-overlapping areas. These areas are "vital patient data" area 110, an "alarm message" area 120, an "information area" 130 and a "controls" area 140. Area 130 is a multipurpose area that maybe used to display, for example only, screens depicting current alarms, an alarm history log, real-time waveforms, measured patient data that is not otherwise displayed in the vital patient data area 110, quick reference information, a log of diagnostic codes, operational time for system components, a ventilator test summary, the current ventilator software hardware configuration, a log of the results from running a short self test, apnea ventilation settings and safety ventilation settings.

Similarly, the lower display 70 is divided into five non-overlapping areas. These areas are a "main settings" area 150, an "information area" 160, a "controls" area 170, a "symbol definition" area 180 and a "prompt" area 190. Examples of information displayed in area 160 include, but are not limited to screens displayed during ventilator startup and ventilator setup, apnea setup, alarm setup, new patient setup, communications setup, date/time setup, miscellaneous setting not otherwise shown in the main settings area 150 and breath timing graphs.

It will be understood that the labeling of the four non-overlapping areas of the upper display 60 and the labeling of the five non-overlapping areas of the lower display 70 are not critical to the present invention, but are for convenience only. Thus, the areas could have other labels, depending on the information desired to be conveyed.

The display area also includes an alarm display area generally indicated by reference numeral 108. The alarm display area 108 includes a high urgency alarm indicator 110, a medium alarm urgency indicator 112 and a low urgency alarm indicator 114. The alarm urgency indicators 110, 112 and 114 may be light emitting diodes or any other means of providing a visual indication of an alarm. Additional indicators (not shown) may also be included below the alarm indicators.

Low urgency alarms are used to inform the user that there has been some change in the status of the patient-ventilator system. During a low urgency alarm, the low urgency alarm indicator 114 lights, an audible alarm having a tone indicating that a low urgency alarm event has occurred, and an alarm message is displayed in the alarm message area 120 of the upper screen 60. During a medium urgency alarm, the medium urgency alarm indicator lights, a medium urgency audible alarm is sounded, and an alarm message is displayed in the alarm message area 120 of the upper screen 60. Because medium urgency alarms typically require prompt attention to correct the cause of the alarm, the medium urgency indicator may flash, and the audible alarm may sound repeatedly with a distinctive tone.

High urgency alarms require immediate attention to ensure patient safety. During a high urgency alarm, the high urgency indicator 110, which may be colored red, flashes, a distinctive audible alarm is sounded and an alarm message is displayed in the alarm message area 120 of the upper screen 60.

Figure 4:
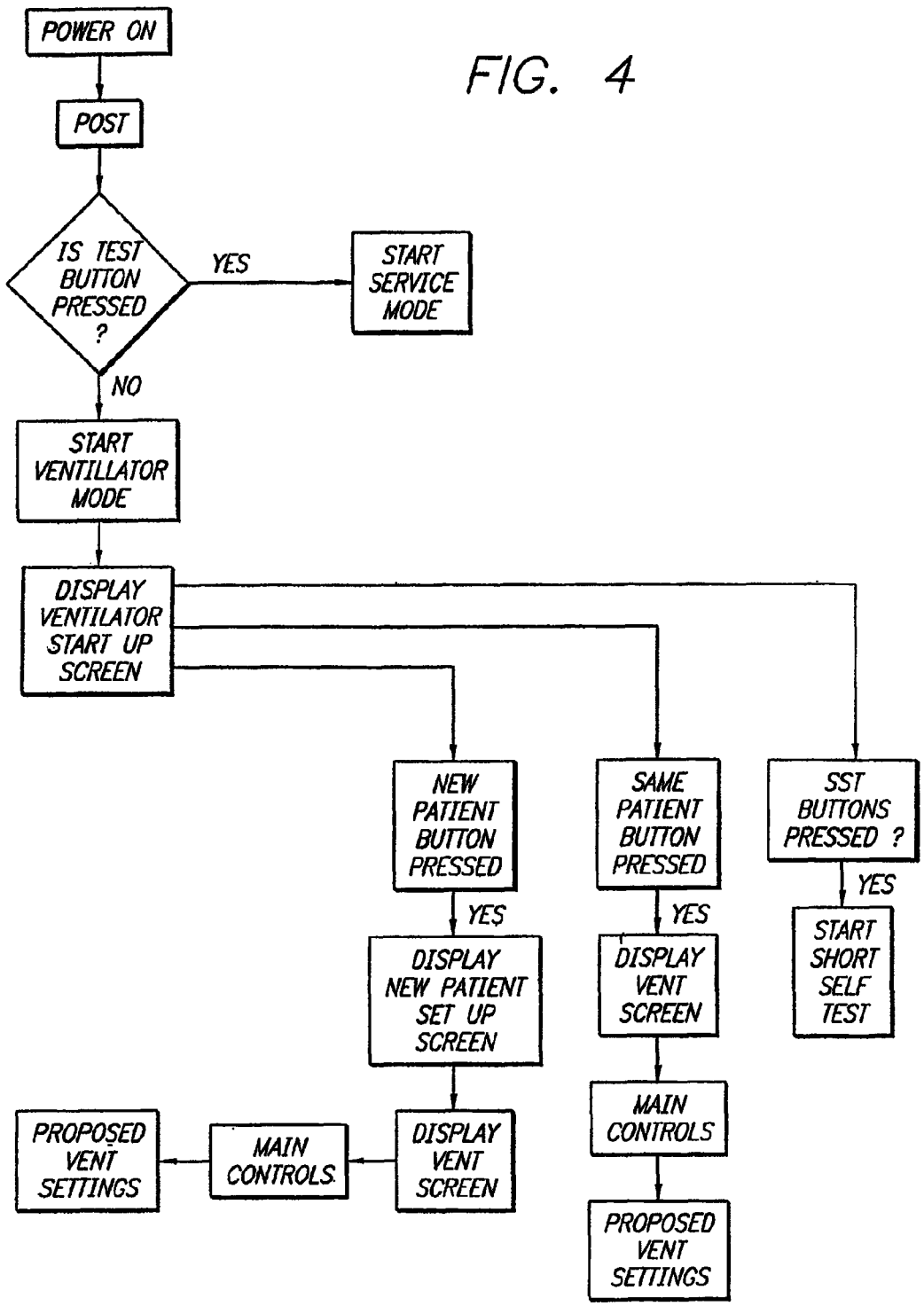
FIG. 4 is a schematic diagram, primarily in block form of the sequence of display screens typically displayed by the graphic user interface of FIG. 3.

Referring now to FIG. 4, the overall hierarchical structure of the user interface comprising the keys, on-screen buttons and upper and lower display screens will be described. When the user of the ventilator turns on the power to the graphic user interface 20 and respirator 22 by actuating a power switch typically located on the respirator 22 (not shown), the processor 30 begins to power itself up by initiating a power on self test (POST). If the user actuates a test button, also typically mounted on the respirator 22 (not shown) during the time when the POST is running, the ventilator will start up in a SERVICE mode. If the test button is not actuated, the ventilator will start up in a VENTILATOR mode.

Figure 5:
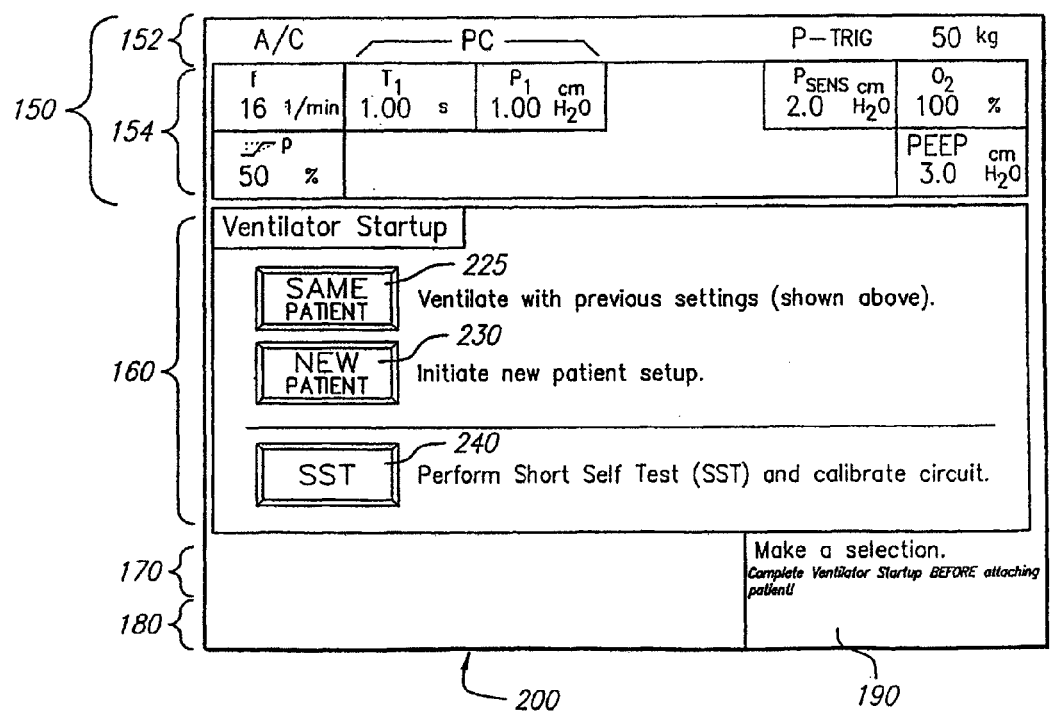
FIG. 5 is an illustration of a ventilator startup screen displayed upon startup of the graphic user interface of FIG. 3.

When the graphic user interface starts up in the VENTILATOR mode, the lower display 70 of the graphic user interface 20 displays the ventilator startup screen 200 depicted in FIG. 5. When the ventilator startup screen 200 is displayed, the main settings area 150 of the lower display has two subareas; the upper subarea 152 displays the main ventilator mode settings, while the lower subarea 154 displays the values of the ventilator settings appropriate to the main ventilator mode settings that were in use prior to powering down the graphic user interface 20 and respirator 22.

The control area 170 on the lower screen 70 typically contains one or more on-screen buttons (see FIG. 8), but is blank on the ventilator startup screen 200, as illustrated in FIG. 5. This illustrates the dynamic nature of the various screens that are presented to the user to assist the user in selecting ventilator settings appropriate to a given respiratory strategy. At this stage of the startup process, no settings other than those illustrated are presented to the user so that the user may not inadvertently enter an inappropriate ventilator setting. Other novel features of the display of the present invention further assisting the user will be described below.

A message instructing the user as to what action to take next is displayed in the prompt area 190. As indicated by the message displayed in the prompt area, it is important that the ventilator be setup before attaching the ventilator to a patient.

As is illustrated by display depicted in FIG. 5, on-screen buttons such as buttons 225, 230 and 240 that are active and may be touched by the user to initiate activity are displayed so that the on-screen buttons appear to have a raised, three dimensional appearance. In contrast, on-screen buttons whose actuation is not appropriate on a particular screen are displayed having a flat, non-three dimensional appearance, as, for example, the on-screen buttons displayed in subarea 154 of the main settings area 150.

The information area 160 of the ventilator startup screen 200 provides the user with three on-screen buttons to choose from to initiate the next step in completing the setup of the graphic user interface 20. The user may touch the SAME PATIENT on-screen button 225 followed by the off-screen ACCEPT key 10.4 to set up the ventilator with the settings displayed in the main settings area 150. If no previous patient settings are stored in the memory 35, the SAME PATIENT on-screen button will not be displayed. Alternatively, if the ventilator is being used to provide respiratory therapy to a patient different from the previously treated patient, the user may actuate the NEW PATIENT on-screen button 230. Actuation of the NEW PATIENT on-screen button 230 will result in the display of a new patient setup screen. The user may also choose to perform a short self test (SST) of the ventilator and the graphic user interface 20 by touching the SST on-screen button 240. The SST on-screen button 240 will not be displayed if the ventilator is already connected to a patient.

The upper display 60 and the lower display 70 incorporate touch sensitive screen elements, such as, for example only and not by way of limitation, infrared touch screen elements, to allow for actuation of on-screen buttons, such as on-screen buttons 205, 210, 215, 220, 225, 230 and 240. The touch screen elements and the processor 30 operate in coordination to provide visual cues to the user as to the status of the on-screen buttons. For example, as described previously, the on-screen buttons are displayed in such a manner as to appear to be three-dimensional. When one of the on-screen buttons is actuated by the user touching the display screen with a finger, a pencil or other instrument, the touch screen elements detect the application of the finger, pencil or other instrument and provide the processor 3D with signals from which the screen location where the touch occurred may be determined. The processor 30 compares the determined location of the touch with the locations of the various buttons displayed on the current screen stored in the memory 35 to determine the button, and thus the action to be taken, associated with the location of the touch. The processor then changes the display of the touched on-screen button to make the button appear to be depressed. The processor may also alter the display of the text incorporated into the three-dimensional on-screen button. For example, the SAME PATIENT text displayed on the on-screen button 225 normally appears as white letters on a dark or gray button when the button is in an untouched stated. When the button 225 is touched, the processor 30 may cause SAME PATIENT to be displayed as black letters on a white button. Additionally, the prompt area 190 may change to a white background with black letters to draw the user's attention to the prompt area 190 when a message is displayed in the prompt area 190.

Typically, the action initiated by touching an on-screen button is obtained when the user lifts the finger, pencil or other instrument from the surface of the display screen. However, the processor may also be responsive to a user sliding the finger, pencil or other instrument off the on-screen button and onto the remaining surface of the display screen to reset the on-screen button in its un-actuated state and to take no further action. Thus, the action initiated by the touching of the on-screen button may only be obtained when the finger, pencil or other instrument is lifted from the portion of the display screen that is displaying the on-screen button. This feature allows the user to abandon a button touch without activating the function associated with the button in the case where the button was touched inadvertently or in error.

When the NEW PATIENT on-screen button 230 is touched, the processor 30 responds by displaying a new patient setup screen (not shown) and purges any previously entered settings from the memory 35. The new patient setup screen includes an IBW onscreen button for displaying and altering the value for the ideal body weight (IBW) of the patient. The new patient setup screen also includes a CONTINUE on-screen button; however, the CONTINUE button is not displayed until the IBW button is touched to ensure that the user adjusts the IBW to a suitable value. The CONTINUE button is displayed immediately after the IBW button is touched. Thus, if the value for IBW currently stored in the memory 35 is acceptable, the IBW does not need to be adjusted, and the CONTINUE button may be touched to accept the current value of the IBW.

When the IBW on-screen button is touched, the value for IBW currently stored in the memory 35 of the graphic user interface 20 may be adjusted by the user by rotating the knob 106 to either increase or decrease the displayed value until the value for the IBW desired by the user is displayed. The user may then touch the CONTINUE button to store the new value for IBW in the memory 35. When the CONTINUE button is touched, the processor 30 responds by causing a vent setup screen to be displayed. Because the vent setup screen is being displayed in response to the completion of the new patient setup screen, the vent setup screen is displayed in a new patient mode, and is labeled accordingly.

The processor 30 is responsive to the entered value for the patients' IBW to determine the initial values and ranges, or bounds, of the values of the various ventilator settings that are appropriate for use with a patient having that IBW. For example, the range of appropriate values for the various ventilator settings differ between adults and children. The processor will display only values that fall within the appropriate range of values for selection by the user during setup dependent upon the IBW, and will not accept values for settings that fall outside of the determined range: If the user attempts to enter a value outside of the appropriate range for that patient's IBW, the processor 30 may provide an audible indication of an attempt to enter an out of range value and/or a prompt to the user that the value is inappropriate.

Figure 6:
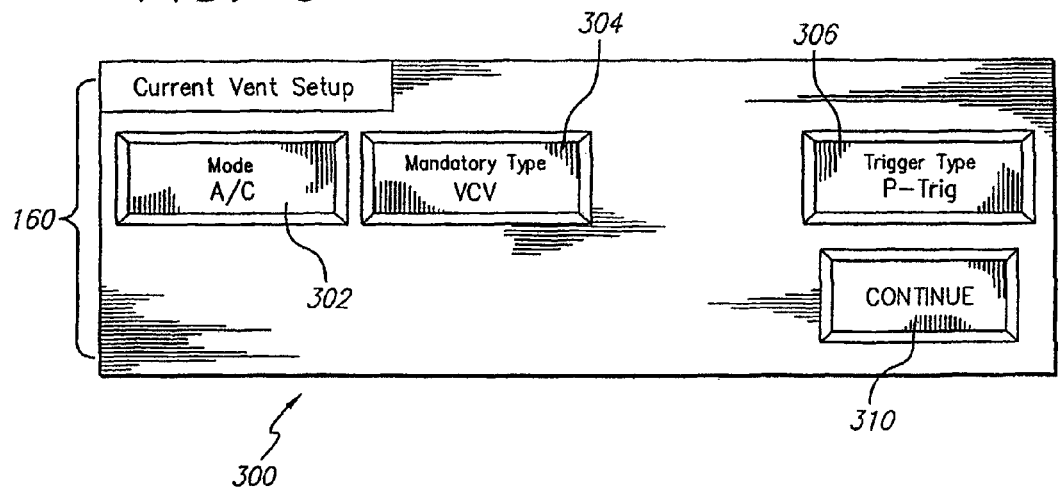
FIG. 6 is an illustration of a main controls setup screen used to set the main control settings of the ventilator of FIG. 3.
Figure 7:
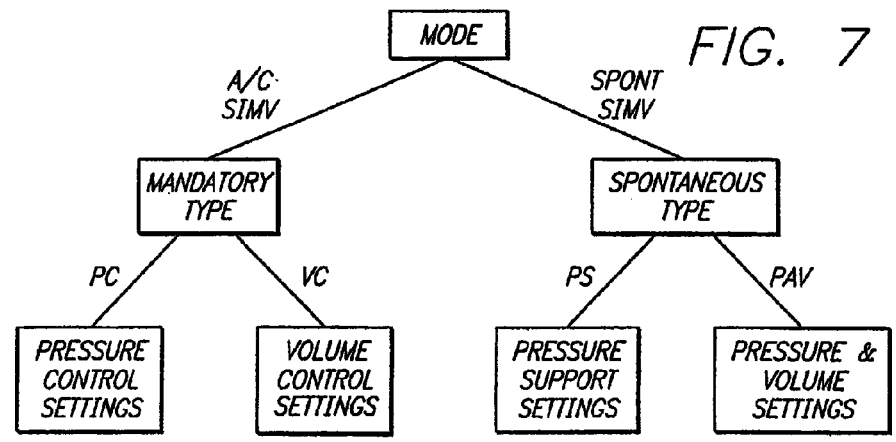
FIG. 7 is a schematic diagram, primarily in block form, illustrating how the adjustment of certain settings affects the applicability of other settings used to control the ventilator of FIG. 3.
Figure 8:
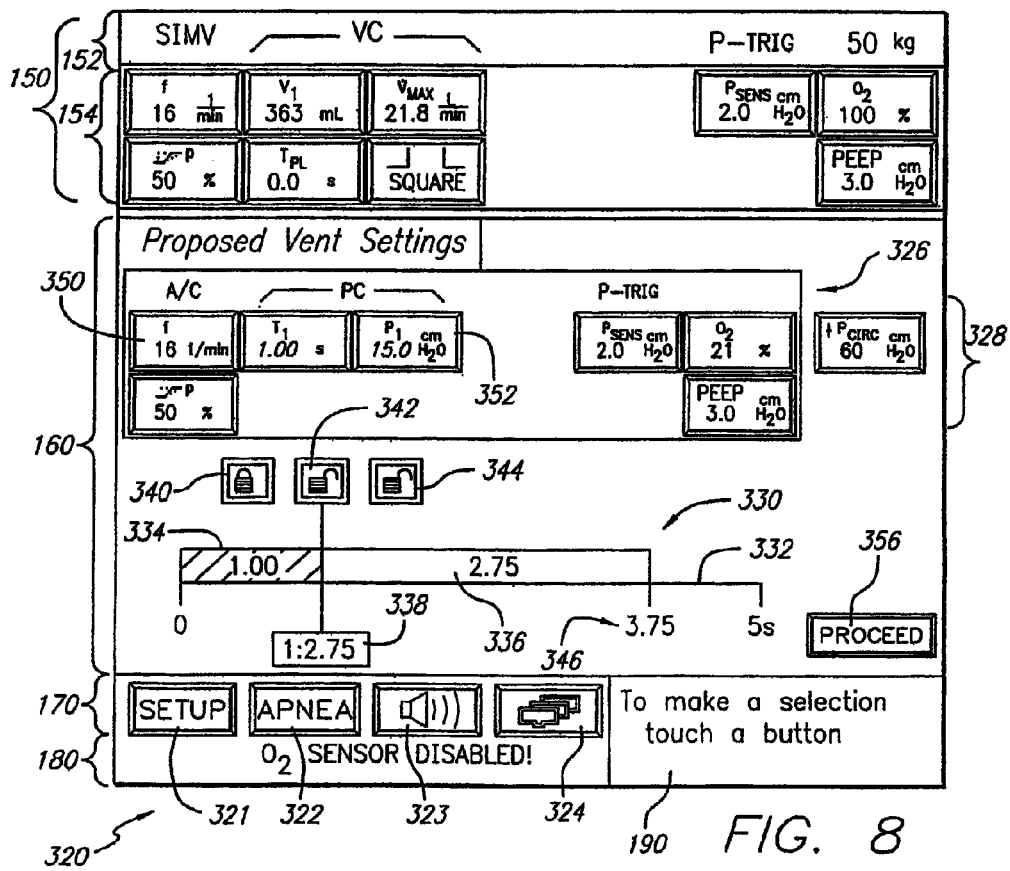
FIG. 8 is an illustration of a proposed vent settings screen including a breath diagram.

Referring now to FIGS. 6-8, the layout and functions of the vent setup screen will now be described. Traditionally, setting up a ventilator required a user to navigate through a number of confusing and complicated displays. A novel aspect of the present invention is the simplification of ventilator setup by hierarchically categorizing the ventilator controls and settings to minimize the number of choices available to a user on anyone screen. The vent setup sequence used to configure the ventilator comprises two display phases. These two phases have been designed to simplify setup of the ventilator by grouping ventilator settings in logically arranged groups. Further, the settings entered during the first phase determine the settings presented to the user during the second phase. In this manner, only those ventilator parameters that are appropriate for the mode settings entered during the first phase are displayed. Additionally, the ranges of values, or bounds, of the displayed settings may be further limited as appropriate depending on the proposed ventilator mode and settings. Moreover, since some ventilator parameters may be dependent on the values selected for certain other ventilator parameters, the ranges of values for the dependent ventilator parameters may be limited in accordance with the settings of those independent ventilator parameters. In this manner, the user is presented only with those settings that are appropriate depending on settings already entered by the user. Such a hierarchical sequencing and presentation are useful in preventing the inadvertent entry of inappropriate ventilator settings.

Once a value for IBW has been entered, the subsequent phases of the New Patient Setup process are similar to the "Vent Setup" sequence of screens which may be accessed at any time during normal ventilation by touching button 321 (FIG. 8). For example, in the first phase of New Patient Setup, a screen is displayed entitled "New Patient Setup" instead of "Current Vent Setup" and is preceded by a screen presenting the proposed setting for IBW. Similarly, in the second phase, the title of the screen is "New Patient Settings" instead of "Current Vent Settings." Accordingly, the following discussion address the "Vent Setup" sequence.

When the vent setup screen is first activated, or following the IBW screen utilized during the new patient setup procedure described above, the Main Controls phase depicted in FIG. 6 is displayed. In the Main Controls phase, only buttons 302, 304 and 306, representing the main control settings, are visible in the information area 160 of the lower display screen 70. As shown in FIG. 8, however, the values for the currently selected main controls continue to be displayed in area 152, and the currently selected settings are display in area 154 of the main settings area 150 of the lower screen 70. The values displayed in areas 152 and 154 remain visible at all times during ventilation setup; thus it may be assumed that they are displayed unless specific reference is made to the display of different information in areas 152 and 154. When the main controls screen is being displayed during the "New Patient Setup" sequence, the on-screen buttons in area 154 of the main settings area 150 are displayed with a flat, non-three dimensional appearance, indicating that they cannot be actuated. During normal ventilation however, the on-screen buttons in area 154 may always be actuated by the user; thus they are displayed with a raised, three-dimensional appearance during normal ventilation.

As depicted in FIG. 7, the present invention decomposes the traditional mode setting into a simple mode plus separate "mandatory type" and "spontaneous type" settings. There are three modes: "A/C", or assist/control mode; "SIMV" or synchronous intermittent mandatory ventilation; and "SPONT", for spontaneous respiration. Dependent on the mode and type selected, the processor 30 will display only those settings appropriate to that mode and mandatory type. For example, if the user selects "A/C" mode and "PC" mandatory type, the processor 30 will display on-screen buttons for changing ventilator settings related to pressure control of the ventilation. Similarly, selecting "SPONT" mode and "PS" spontaneous type results in the display of on-screen buttons for changing ventilator settings related to pressure support.

Referring again to FIG. 6, Button 302 is labeled with "Mode"; Button 306 is labeled with "Mandatory Type"; and Button 306 is labeled with "Trigger Type." Each of the buttons 302, 304 and 306 also display the setting currently selected for each of the main control settings. For example, button 302 displays "A/C" indicating that assist/control mode is selected. Alternatively, where SIMV or SPONT modes are currently selected, button 302 will display either SIMV or SPONT as appropriate. When either SIMV or SPONT modes are currently selected, a fourth button, button 308 (not shown) labeled with "Spontaneous Type" may also be displayed. Further, when the mode is set to SPONT, a message may be displayed below button 304 indicating that the value displayed on button 304, "Mandatory Type," applies to manual inspiration only.

As with others of the buttons used to make changes to the values of various operational parameters used by the processor 30 to control the respiratory therapy of a patient, the main control settings on the current vent setup screen are set by touching the desired one of the displayed buttons 302, 304, 306 or 308 (not shown), and then rotating knob 106 until the desired value is displayed. When the desired value for the setting is displayed, the user may provisionally accept and store that value in the memory 35 by touching the continue button 310. Alternatively, if more than one main control setting needs to be changed by the user, the user may defer touching the continue button 310, and may instead select among the other buttons to change the values of a different main control settings. The user may, if so desired, change the values of each of the main control settings. When the user has changed all of the desired main control settings, the changed values for each of the main control settings may be provisionally accepted, pending completion of the second phase of the ventilator setup procedure, and stored in the memory 35 simultaneously by touching the continue button 310. Thus, the values for the main control settings may be accepted and stored in a batch, rather than one setting at a time. This is advantageous in that entry of multiple settings is easier and less time consuming. Batch entry is also useful in that all of the proposed values for the main control settings are displayed, and may be checked for entry errors by the user before being committed storage in the memory 35.

When the continue button 310 is touched, the first phase of ventilator setup is complete and the second phase begins. In the second phase of ventilator setup, the processor 30 displays a proposed vent settings screen 320 to prompt the user to complete the vent settings phase of the setup procedure, as depicted in FIG. 8. The proposed vent settings screen is displayed in the information area 160 of the lower display 70 (FIG. 3). This screen includes a display 326 of the main control settings set in the first phase described above, and an area 328 where a plurality of buttons are displayed. The buttons displayed in the area 328 are for setting the values for particular ventilation parameters that are appropriate to the main control setting. Thus, the buttons displayed in area 328 are dependent upon the values selected for the main control settings in the first phase of the ventilator setup. This display of only those buttons whose settings are appropriate to their associated main control settings simplifies the display, thus aiding the user in setting up the ventilator and preventing inadvertent errors due to user confusion.

As with the main settings screen displayed during the first phase of the vent setup procedure, the user may select a parameter to change by touching one of the on-screen buttons, such as the "$P_1$" on-screen button 352. When the user touches button 352, the button appears to be depressed, and may change color and text contrast as described above. The user then adjusts the value of the setting by turning knob 106 (FIG. 3) until the desired value is displayed on the button 352. If the user is satisfied with the value entered for button 352, and the other displayed values, the user may touch the PROCEED button 356, followed by the ACCEPT key 104 (FIG. 3) to complete the vent setup procedure. Alternatively, the user may touch another one of the on-screen buttons, such as the "f" on-screen button 350. When button 350 is touched, button 352 "pops" up, indicating that button 352 is no longer selected, and button 350 appears to become depressed. An audible indication that the button is touched, such as a "click" may also be provided. In this manner, the values for all of the settings displayed may be changed one after another if desired, or only certain of the settings may be changed, as desired by the user. The user then may configure the ventilator to operate in accordance with all of the changed settings at once in a batch fashion by touching the PROCEED on-screen button 356, followed by pressing the off-screen ACCEPT key 104.

FIG. 8 further illustrates additional aspects of the graphical features provided by the user interface 20 that assist the user in setting up and operating the ventilator. As depicted in FIG. 8, the main settings area 152 displays the currently active main settings. These settings are easily compared with the main settings entered during the first phase of setup that are now displayed on the proposed vent settings screen in area 160. For example, as illustrated in FIG. 8, the ventilator is currently setup to ventilate in the SIMV mode, and the user has provisionally changed the mode to A/C, as indicated in the display 326. Another aspect of the invention is the visual prompt provided to a user that a particular setting has been changed. This aspect is illustrated by the change in the font used to display the value of the setting for "$P_1$" where the value "15.0" is displayed in italics, indicating that this value has been changed, compared to the normal font used to display the value "16" for "f", indicating that this value has not been changed.

If any of the main settings were changed during the first phase of the vent setup procedure were changed, the PROCEED on-screen button 356 is displayed on the proposed vent settings screen 320. Similarly, if none of the main settings were changed, the PROCEED on-screen button is not displayed until one of the settings displayed during the second phase of the vent setup procedure is changed. If the user is satisfied with the values for the settings that have been entered, the user may touch the PROCEED on-screen button 356. The user may then complete configuration of the ventilator settings, replacing the current vent settings with the proposed settings, by pressing the off-screen ACCEPT key 104. The off-screen placement of the ACCEPT key 104 ensures that no inadvertent changes are made to the ventilator settings.

If the processor 30 determines that the vent setup screen has been activated within a predetermined short period of time, for example, within 45 minutes of the most recent time the vent setup screen was used to change values of the ventilator settings, the processor 30 may display a PREVIOUS SETUP button on the main settings screen 300 (FIG. 6). The processor 30 removes this button from the screen if any changes are made using the screen. If the user touches the PREVIOUS SETUP button (not shown) on the main 30 settings screen, a screen similar to the second phase display depicted in area 160 (FIG. 8) is displayed, showing values for the settings as they were immediately prior to the last setting change made using the vent setup screen. The on-screen settings buttons are all displayed in the flat, non-three dimensional state, indicating that they cannot be adjusted. A prompt message is displayed in area 190 explaining that accepting the displayed values will result in the entire previous setup being restored, including old alarm and apnea settings. The previous setup may be re-instated by the user by touching the PROCEED button 356, followed by pressing the ACCEPT key 104. This feature of the present invention allows a user to quickly restore the ventilator to the settings state it was in prior to a major setup change in the event that the altered ventilation strategy is not successful. A time line is placed on the availability of the previous settings to avoid the possibility of re-imposing the settings when the patient's condition may have changed substantially. Individual changes to settings may be made to settings in the period following a major settings change without invalidating the settings stored for the previous setup. However, batch changes, that is, the changing of more than a single setting at a time, results in the stored previous settings being replaced with the most recent set of settings. This provides the user with the ability to fine tune the settings made during the major change without losing the ability to "UNDO" all of the major changes and return to the previous settings.

Referring again to FIG. 8, the proposed vent settings screen 320 also includes a graphical representation, or breath diagram 330, of the breath cycle that will be provided to the patient based on the settings entered by touching the buttons displayed in area 328 and adjusting the resulting displayed values using the knob 106, as described above. The breath diagram 330 includes a time line 332 that is displayed for scale purposes only, an inspiration bar 334 indicating the portion of the total breath duration during which inspiration will take place, an expiration bar 336 indicating the portion of the total breath duration during which expiration will take place, an inspiration/expiration ratio display 338 and a total breath time display 346. Besides the graphical representation of the duration of the inspiration and expiration portions of the total breath cycle, text representing the selected value for the durations may be displayed in the respective bars 334 and 336. For example, the inspiration phase of the breath is set to require 1.0 seconds and the expiration phase is set to require 2.75 seconds. The colors or shading of the inspiration bar 334 and the expiration bar 336 are preferably different to facilitate a user distinguishing between them. For example, the inspiration bar 334 may be shaded dark with white text, indicating that the breath timing parameter is "locked", while the expiration bar 336 may have grey shading and black text. It will be understood that this color scheme is only one example of a variety of color schemes that may be used to enhance the graphical representation of the breath cycle to provide a readily comprehensible display of either the current status of the ventilation or to assist a user in evaluating the effects of proposed changes to the ventilator settings.

Lock on-screen buttons 340, 342 and 344 are displayed above the time line 332 and display the lock status of the settings for the inspiration bar 334, the inspiration/expiration ratio 338 and the expiration bar 336 respectively. The user may change the lock status of the settings by selecting and touching one of the lock icons 340, 342, 344. For example, lock button 340 displays a graphical representation of a closed, or locked, padlock, while lock buttons 342 and 344 display graphical representations of open, or unlocked, padlocks. Touching lock button 340 will result in the lock button changing to the open, or unlocked state. Similarly, touching lock buttons 342 or 344 will result in the touched lock button changing to the closed, or locked, state. The effect of the "locked" setting is that the setting will not be automatically changed in accordance with a subsequent change in the breath rate parameter, while both of the settings for the "unlocked" parameters, here, the expiration time and the ration of inspiration to expiration, will be changed.

The display of the lock buttons is dependent upon the selected main control settings. For example, in the representative example depicted in FIG. 8, main control setting Mandatory Type is set to "PC", thus causing the lock buttons to appear; if the Mandatory Type is set to "VC", the lock buttons would not be displayed. When the Mandatory Type is "PC", only of the three "breath timing" settings, $T_1$, $T_E$ or I:E is displayed. $T_1$ is set by touching the on-screen button labeled $T_1$, and adjusting the knob 106 until a desired value is displayed. The value will be displayed both on the on-screen button $T_1$, and in the inspiration bar 334 of the breath diagram 330. Because the value for $T_1$, is locked, as evidenced by the closed lock button 340, and the dark shading of the inspiration bar 334, changes to the breath rate do not result in a change to the inspiration time; only the expiration time, inspiration/expiration ratio and the total breath time change. If another time parameter, such as $T_E$ was locked, changes to the rate would not affect $T_E$ but $T_1$ and the inspiration/expiration time ratio would change.

Figure 9A:
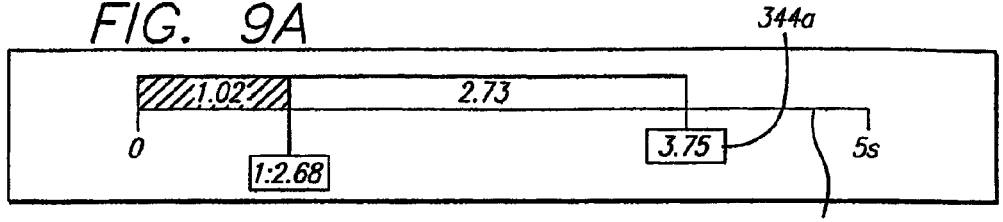
FIGS. 9A, 9B, and 9C are illustrations depicting the display of the breath diagram of FIG. 8 dependent upon the values of the parameters represented by the breath diagram.
Figure 9B:
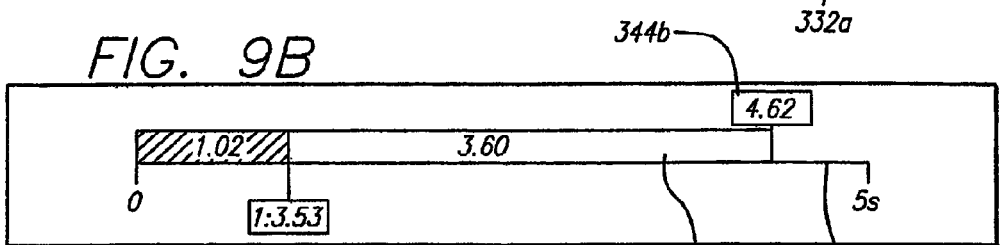
Figure 9C:
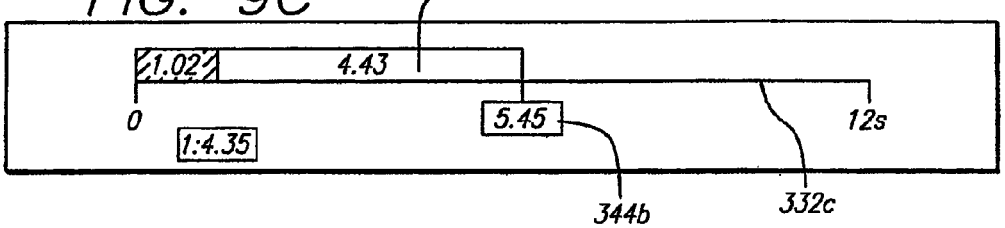

The above described relationship is apparent from FIGS. 9A-C. In FIG. 9B, the breath rate has been reduced; thus, the total breath time is increased, as indicated by the value in total time display 344*b*. Since the value for the inspiration time was locked, the relative length of the inspiration bar 334*b* did not change, while the relative length of the expiration bar 336*b* increased. A novel aspect of the present invention evident from the display depicted in FIG. 9B is the change in the location of the total breath time display 344*b*. In FIG. 9A, the total breath time display 344*a* is located below the time line 332*a*. In FIG. 9B, the expiration bar 336*b* has grown larger because of the increased breath time to the extent that the total breath time display 344*b* has approached the end of the time line 332*b*. The processor 30 maintains the location of each of the graphical features of the displays in the memory 35, and constantly assesses whether the display of a graphical feature, such as the breath diagram 330, on-screen buttons or text may possibly collide or overlap. In the case depicted in FIG. 9B, the processor 30 determined that the total breath time display 344*b* would be displayed sufficiently close to the end of the time line 332*b* that the total breath time display 344*b* would interfere with the display of the numerical scale of the time line 332*b*. Accordingly, the processor caused the total breath time display 344*b* to be displayed above the time line 332*b* to avoid such interference. It will be understood that the use of the total breath time display 344*b* is for purposes of example only. Any of the text or numeric values displayed in conjunction with the breath timing diagram 330 may be displayed as necessary to prevent interference with other graphical elements.

The processor 30 is also responsive to the values of the setting to change the scale of the time line 332 when appropriate. As depicted in FIG. 9C, the total breath duration 344*c* has been increased again, and is now greater than the previous scale of the time line 332*c*. Accordingly, the processor 30 has caused the time line 332*c* to be displayed with a larger scale. As the scale of the time line 332*c* enlarges, the relative lengths of the inspiration and expiration bars 334, 336 also change. As was described above, if the relative length of the inspiration bar 334*c* becomes too small to allow the display of the value of the inspiration time setting within the bar as depicted, the processor may cause the value to be displayed either above, below or to the left of the time line 332*c* in the vicinity of the inspiration bar 334*c*.

One advantage of a preferred embodiment of the invention is that the main control settings are displayed on both the vent setup screen and in the main setting area of the 152 of the lower display 150. Thus a user may adjust the main settings using either screen. However, it is particularly advantageous to make adjustments to the main control settings using the vent setup screen because only one main setting at a time may be changed in the main settings area 152, while multiple changes may be made in the vent setup screen and then accepted by the user and stored in the memory 35 of the graphic user interface 20 by the user as a batch.

Figure 10:
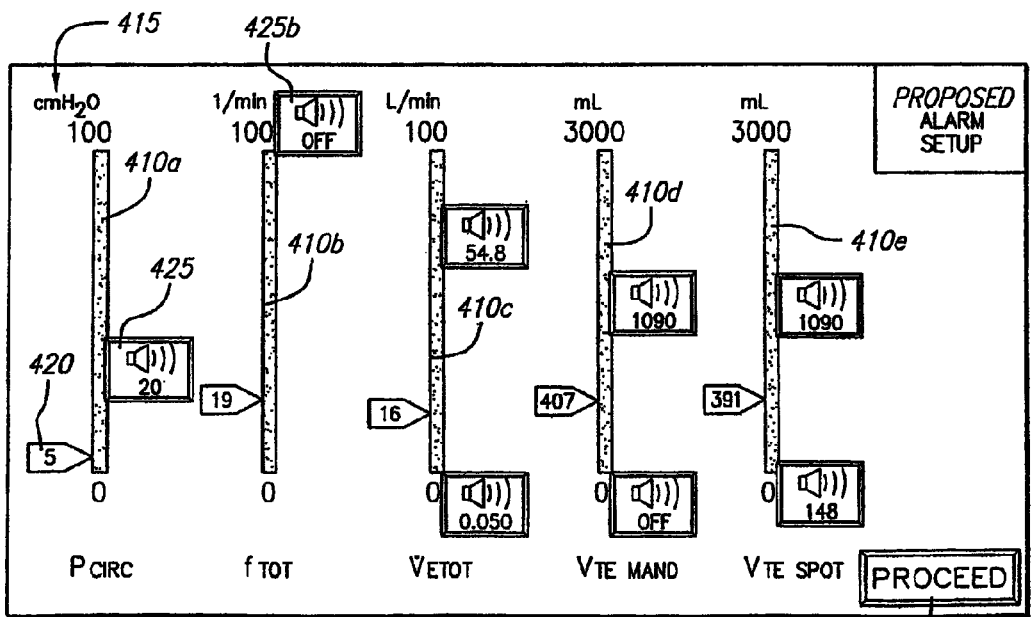
FIG. 10 is an illustration of an alarm setup screen including graphical representations of various alarms settings, acceptable alarm setting parameter ranges, and current patient data.

Referring now to FIG. 10, the alarm setup screen will be described. Touching the "Alarms" button 215 (FIG. 5) on the lower screen 70 causes the processor 30 to display the alarm setup screen 400. The alarm setup screen 400 displays graphical representations for those user-adjustable alarms that are appropriate given the values selected for the main control settings. Thus, a user may be presented only with alarm settings required by the ventilation strategy already entered and stored in the memory 35 of the graphic user interface 20. This facilitates setup and prevents errors or omissions due to information overload given the relatively small size of the information display area 160 on the lower screen 70 of the graphic user interface 20.

Ease of use is further enhanced in that each graphical representation 410a, 410b, 410c, 410d and 410e of an alarm includes a label 415 identifying the patient data parameter associated with the alarm and a display 420 of its current value. The value for the alarm setting associated with particular patient data parameter setting is displayed on an onscreen button 425. To further enhance the usefulness and comprehensibility of the graphical representations 410a, 410b, 410c, 410d and 410e, the processor 30 causes the alarm on-screen button 425 to be displayed at a location along the graphical line that is proportional to the value of the setting with respect to total length of the graphical line.

The user may adjust the setting of each of the displayed alarm settings by touching a selected alarm on-screen button, such as alarm button 425, and then rotating the knob 106 (FIG. 3) until the desired alarm setting is displayed on the alarm button 425. As the value for the alarm setting is changed by rotating the knob 106, the processor changes the position of the alarm button 425 along the graphical line, providing a visual display of the change to the user. The position of the displayed patient data parameter 420 is similarly adjusted.

Certain alarm settings may also be turned off so that no alarm sounds for selected control settings. One possible display of an alarm in the off state is shown by the location and display of the alarm on-screen button 425b.

Some patient data parameters may require the setting of both upper and lower alarm limit values defining a range of acceptable values beyond which a user desires an alarm to be given, as is depicted by the graphical representation 410c. Alternatively, as depicted by the graphical representation 410d, a lower limit alarm may be turned off by the user, while setting an upper limit alarm to a selected value. Similarly, the upper limit alarm may be turned off while a value for a lower limit alarm is set. When all of the alarms are set, the user may store the values for one, or all of the alarm settings in a batch manner by touching the PROCEED button 430 followed by pressing the off-screen ACCEPT key 104.

Figure 11:
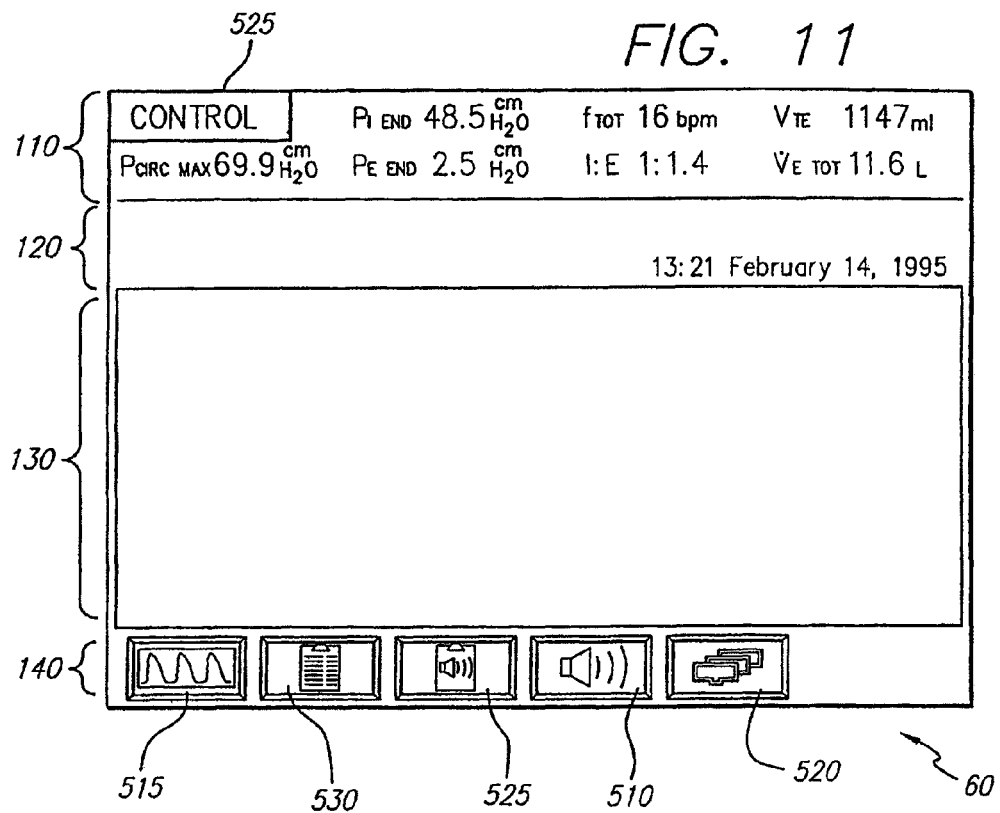
FIG. 11 is an illustration of the upper display screen of FIG. 3.

Referring now to FIG. 11, one exemplary layout of the upper display screen 60 of the graphic user interface 20 will now be described. As described above, the upper display screen 60 includes four non-overlapping areas 110, 120, 130 and 140. Generally, the upper display screen 60 provides a user with information regarding the state of the current ventilation therapy. Vital patient information is displayed in the vital patient information area 110. The information displayed in area 110 is always displayed when ventilation is in progress, even while the lower display screen 70 is being used to modify the settings controlling the ventilation. One novel aspect of the present invention is the display of the current breath type and breath phase in the breath type area 525 shown located in the upper left corner of the vital patient data area 110. In addition to the "CONTROL" breath type displayed, the ASSIST OR SPONT breath types may be displayed in accordance with the values for the main settings set as described above. The breath phase, that is, inspiration or expiration, is indicated by alternately reversing the display of the breath type in the breath type area 525. For example, the text displayed in the breath type area 525 may be displayed as black letters on a white background during the inspiration phase, and as white letters on a black background during the expiration phase.

It is not unusual during the course of a ventilation treatment session for values of monitored parameters to exceed the limits set for the various alarms that may be active during the session. The processor 30 receives signals from the sensors 27 (FIG. 2) for a variety of monitored parameters through the interface 32 and compares the values of those inputs to the values associated with the alarm settings stored in the memory 35. When the processor determines that the value of an input violates the value or values for the limit or limits for a particular alarm setting associated with that input stored in the memory 35, the processor 30 may cause an audible alarm to be sounded, and displays a text prompt identifying the monitored parameter, the cause of the alarm and a proposed course of action to correct the out of limit condition in the alarm messages area 120. If an event occurs that is potentially harmful to the patient, the processor 30 may also control the ventilator to abort delivery of the current breath until a user may intervene and correct the condition causing the alarm.

Many alarm conditions, however, may exist that do not require immediate correction, but are useful to evaluate the course of the respiratory treatment. Accordingly, all alarms are accumulated in an "Alarm Log" that is a chronological listing of all alarms that have occurred and which may be reviewed in area 130 of the upper screen 130 (FIG. 3) at any time during or after respiratory treatment. If, for some reason, the alarm log contains records of alarm conditions than may be conveniently stored for latter viewing, the processor 30 may cause the oldest alarm records to be deleted, and thus they will not be available for viewing.

Figure 12:
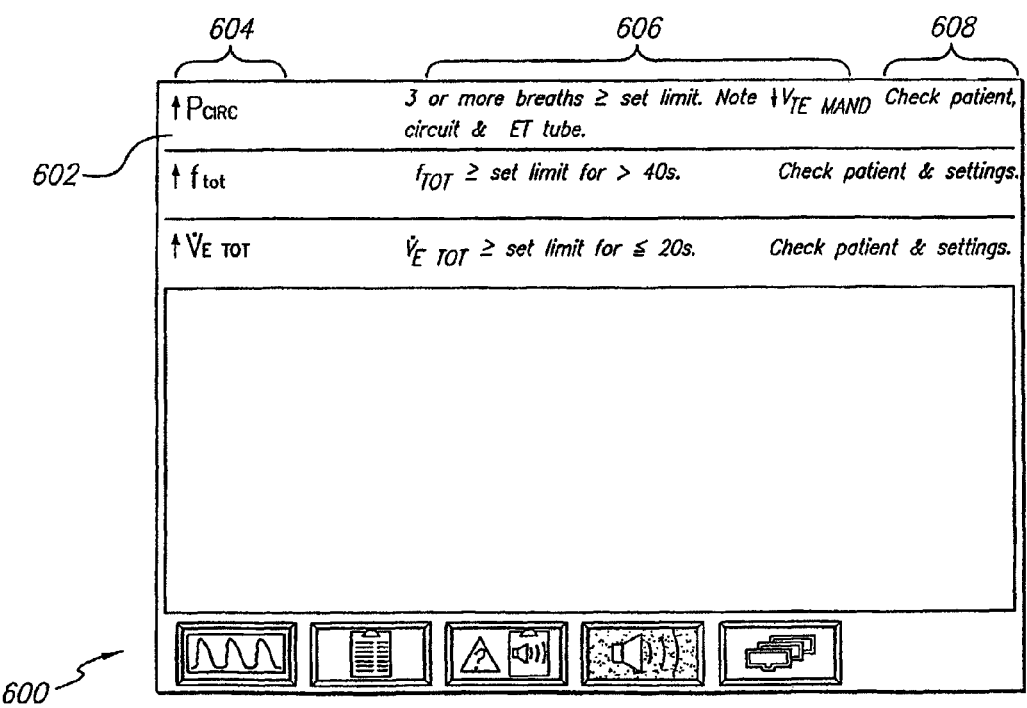
FIG. 12 is an illustration of a "More Alarms" display screen displayed within the information area of the display screen of FIG. 11.

If multiple alarm conditions occur during the course of treatment, the number of alarm messages may exceed the display area available in the alarm message display area 120. The processor 30 may display those alarms having the highest priority in the display area 120, scrolling alarms having a lower priority off the screen. The user may review alarms having a lower priority by touching the "More Alarms" button 510 displayed in the controls area 140. The scrolled alarm messages are displayed in the information area 130 of the upper screen 60. When the "More Alarms" button 510 is touched, the upper screen 60 is temporarily re-arrange to merge areas 130 and 120 into a combined and larger active alarms display, as depicted in FIG. 12. Touching the "More Alarms" button 510 again causes the processor 30 to redisplay the default screen display depicted in the FIG. 11.

Each alarm message 602 (FIG. 12) includes three messages to assist the user in correcting the cause of the alarm. A base message 604 identifies the alarm. As will be described more fully below, the user may touch the alarm symbol to display a definition of the alarm symbol in the symbol definition area 180 of the lower screen 70 (FIG. 3). An analysis message 606 gives the root cause of the alarm, and may also describe dependent alarms that have arisen due to the initial alarm. A remedy message 608 suggest steps that can be taken by the user to correct the alarm condition.

As illustrated above, the processor 30 may be responsive to user commands to display various kinds of information in the information area 130. For example, FIG. 11 depicts one possible embodiment of the upper screen 60 having five on-screen buttons for causing various information and data to be displayed in the information area 130. Touching "Waveform" button 515 causes the processor 30 to display a graphical plot of the data pertinent to the respiratory therapy being given to the patient. Similarly, touching the "More Data" button 530 results in the processor 30 displaying a screen including a variety of data that may be useful to the user in assessing the status of the patient and the progress of the ventilation therapy. It will be understood that the present invention is not limited to including only the five on-screen buttons depicted in FIG. 11. Because the on-screen buttons are implemented by the processor 30, with suitable programming the processor 30 may be enabled to display different or additional on-screen buttons and perform actions in response to their actuation.

Figure 13:
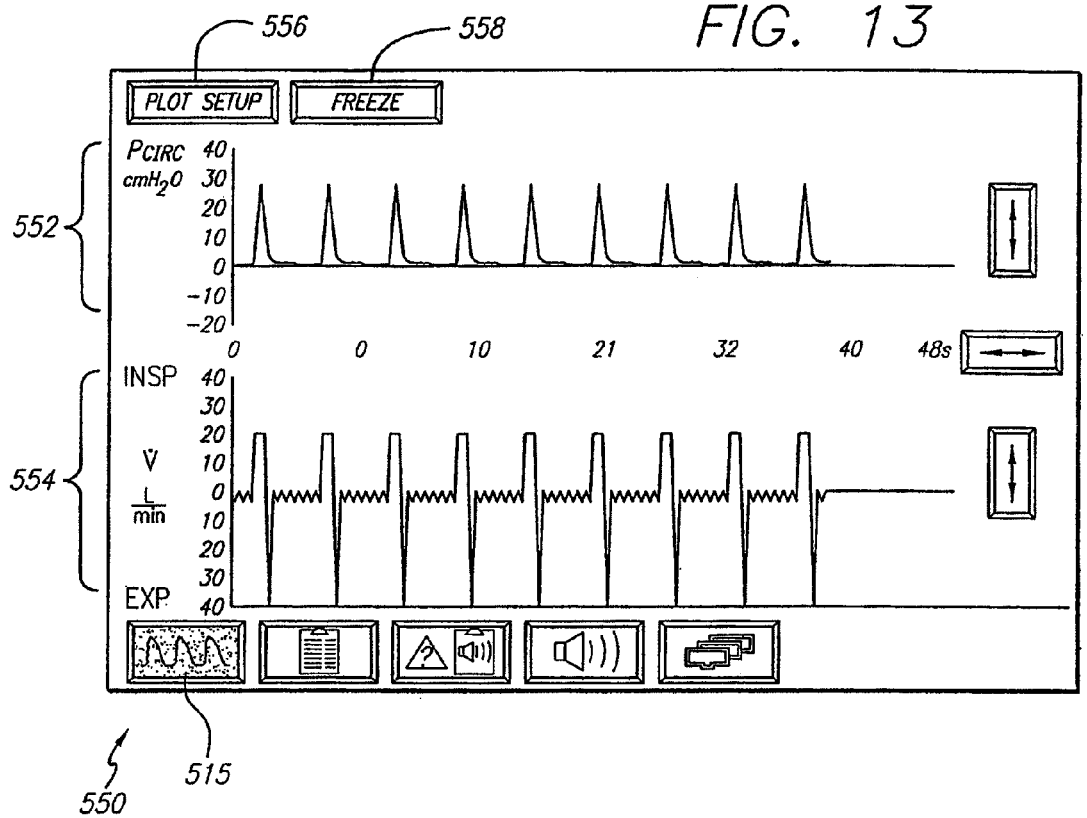
FIG. 13 is an illustration of a "Waveforms" display screen displayed within the information area of the display screen of FIG. 11.

Touching the "Waveform" button 515 displays a waveform display screen 550 as illustrated by FIG. 13. This display allows for real-time plotting of patient data in the tow plots areas 552 and 554. Different plots may be displayed in each of the plot areas 552 and 554. A plot setup screen (not shown) may be accessed by the user by touching the "Plot Setup" button 556. The user may select among plots of pressure versus time, volume versus time, flow versus time and pressure versus volume.

The waveform display screen 550 also includes a "Freeze" button 558 for freezing any waveform that is currently being plotted in either plot area 552 or 554.

Touching button 558 causes a flashing "Freezing" message to be displayed until the current plot is completed and prevents any changes being made to the waveform display screen 550 by causing the various buttons controlling the scale of the displays, as well as buttons 556 and 558 to disappear. The only visible button is an "Unfreeze" button (not shown). When the current plot is complete, plotting stops and the on-screen buttons reappear.

Other displays may also be accessed by touching the on-screen buttons displayed in the controls area 140 of the upper screen 60. For example, touching the "Alarm Log" button 525 causes a screen listing all of the alarm events up to a predetermined maximum number of alarms, including those that have been corrected by the user, that have been sounded during therapy. Touching the "More Screens" button 520 causes the display of a set of additional on-screen buttons giving access to additional data not otherwise presented on the main display screens. This feature provides a flexible way to add new features and screens with minimal impact on the overall design of the graphic user interface.

Figure 14:
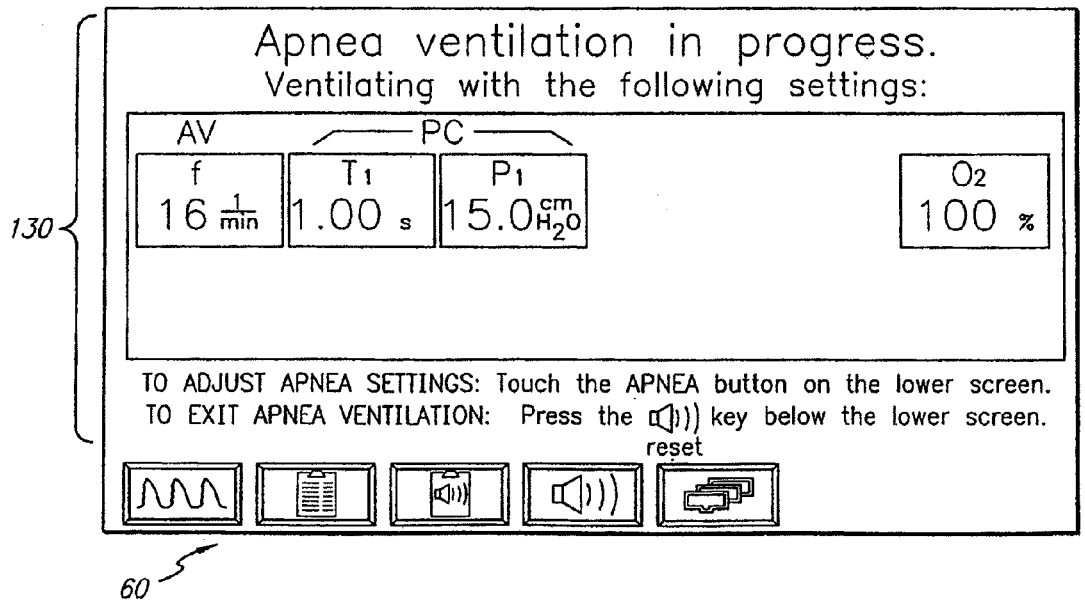
FIG. 14 is an illustration of an "Apnea Ventilation In Progress" display screen displayed within the information area of the display screen of FIG. 11.

In some modes of operation, the respirator processor 60 (FIG. 2) is responsive to signals received from a sensor 27 in the ventilator to provide inspiration. In this manner, the inspiration may be provided when the patient begins to draw a breath in, which is sensed by the sensor and results in the respirator processor 60 causing the ventilator to provide an inspiration. The respirator processor 60 may be programmed to monitor the rate at which a patient triggers the sensor, and, when that rate falls below a predetermined number of breaths per minute, the value of which may be stored in the memory 65 (FIG. 2), the respirator processor 60 sends a signal through the interface 32 to the processor 30 of the graphic user interface 20. In response to this signal, the processor 30 displays an "Apnea Ventilation In Progress" screen 600 in area 130 of the upper display 60, as depicted in FIG. 14. A variety of information may be displayed on this screen to inform the user of the status of the patient and the ventilation. For example, the main control settings and the ventilation settings currently active may be displayed along with a message indicating that apnea ventilation is in progress. Simultaneously, the respirator processor 60 switches to "Apnea" mode and provides breathing assistance to the patient.

Figure 15:
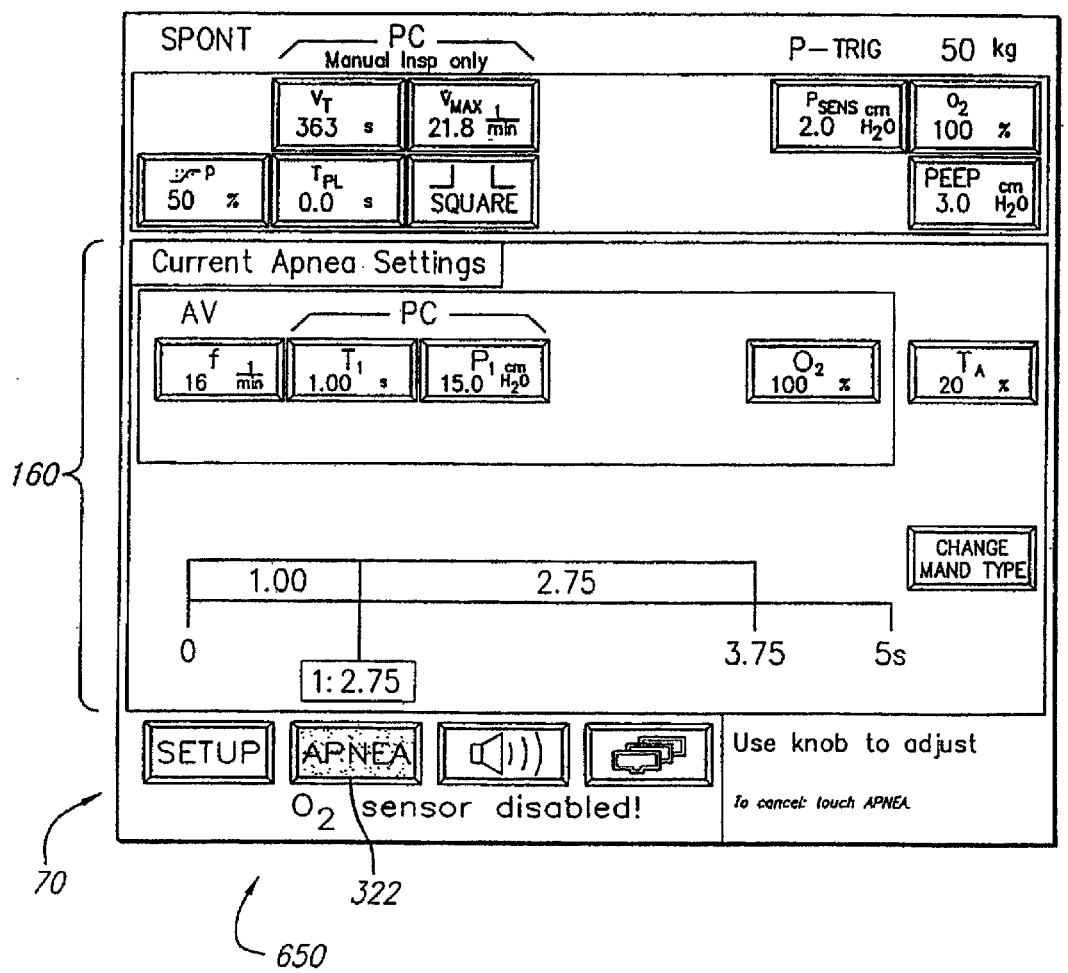
FIG. 15 is an illustration of an "Apnea Settings" display screen displayed within the information area of the lower display screen of FIG. 3.

When the respirator processor 60 automatically institutes "Apnea" mode in response to a lack of inspiration by the patient being treated, the respirator processor 60 controls the apnea ventilation using values of various settings entered by the user from an apnea setup screen 650 that may be displayed in the information area 160 of the lower screen 70 as depicted in FIG. 15 by touching the "Apnea" on-screen button 322 on the lower screen 70 of the graphic user interface 20. One useful feature of the manner in which the processor controls the displays of the graphic user interface is illustrated in FIG. 15. As is shown, the values for the main control settings and the on-screen buttons for setting the ventilation settings appropriate for those main control settings for the ventilation in process when "Apnea" mode was entered are displayed in areas 152 and 154 of the lower display screen (FIG. 5). Additionally, the current apnea settings are displayed in the information area 160, along with on-screen buttons which can be actuated in concert with the knob 106 to adjust the apnea settings.

Referring again to FIG. 5, another novel aspect of the present invention will now be described. The lower display screen 70 includes an area 180 in which the processor 30 may display a variety of messages to assist the user in setting up the graphic user interface. These messages may be different from, or in addition to prompts displayed by the processor 30 in the prompt area 190 of the lower display screen 70. One possible use of the area 180 is to provide a textual definition of a graphic symbol identifying a on-screen button. For example, when a user touches the "Waveform" on-screen button 515 on the upper display screen 60 (FIG. 11), the text "Waveform" may be displayed by the processor 30 in the display area 180. This feature provides the user with an easily accessible means to determine the functionality of any of the graphically identified on-screen buttons on either the upper or lower display screens 60, 70 while allowing the elimination of textual information from the displayed on-screen button to simplify the display.

It is generally an unsafe practice to power-up a ventilator with a patient already attached because the ventilator may attempt to ventilate the patient in a manner which would be harmful to the patient. The respirator processor 60 is responsive to detection of a such a condition to start an "Safety PCV" ventilation mode and to send a signal to the processor 30 of the graphic user interface 20 to sound an alarm. In this mode, the respirator processor 60 controls the respirator 22 using a pre-determined set of ventilator setting in pressure-control mode. These pre-determined settings are selected to safely ventilate the widest set of possible patients. Once the new patient, or same patient setup process is completed as described above, the processor terminates the "Safety PCV" mode, and begins ventilating the patient in accordance with the newly entered settings.

From the above, it will be appreciated that the present invention provides important new capabilities in the display of a graphic representation of a breath cycle for use in evaluating changes to ventilation parameters while using a graphic user interface. While several forms of the invention have been illustrated and described, it will also be apparent that various modifications can be made without departing from the spirit and scope of the invention. Accordingly, it is not intended that the invention be limited, except by the appended claims.

We claim:

1. A patient ventilator system comprising:
   a user interface configured to receive a patient parameter, a ventilator parameter, and an alarm setting for the ventilator parameter, wherein the patient parameter is an ideal body weight for a patient; and
   a processor configured to:
   identify at least one ventilator parameter limit;
   determine at least one alarm setting limit for the ventilator parameter based on the patient parameter, wherein the at least one alarm setting limit is different than the ventilator parameter limit;

compare the alarm setting to the at least one alarm setting limit, wherein the at least one alarm setting limit is representative of at least one value for the ventilator parameter that is not to be exceeded based on the patient parameter;

determine whether the alarm setting exceeds the at least one alarm setting limit; and in response to the determine operation, perform one of accepting the alarm setting or rejecting the alarm setting.

2. The patient ventilator system of claim 1, further comprising:

in response to determining that the alarm setting does not exceed the at least one alarm setting limit, accepting the alarm setting.

3. The patient ventilator system of claim 1, further comprising:

in response to determining that the alarm setting exceeds the at least one alarm setting limit, rejecting the alarm setting.

4. The patient ventilator system of claim 1, wherein rejecting the alarm setting further comprises providing an indication that the alarm setting exceeds the at least one alarm setting limit.

5. The patient ventilator system of claim 1, wherein the at least one alarm setting limit comprises at least one of: an upper alarm setting limit and a lower alarm setting limit.

6. The patient ventilator system of claim 1, wherein the at least one value is preset and included in the instructions of the memory.

7. The patient ventilator system of claim 1, wherein the at least one value is a function of the patient parameter.

8. The patient ventilator system of claim 1, wherein the at least one value is configured to prevent patient distress while allowing alarm settings to be customized for a particular patient.

9. A method for determining whether an alarm setting for a ventilator parameter exceeds at least one alarm setting limit, the method implemented on a ventilator having a processor and a memory with instructions that when executed by the processor cause the ventilator to perform the method, the method comprising:

receiving the alarm setting, the ventilator parameter, and a patient parameter, wherein the patient parameter is an ideal body weight for a patient;

identifying a ventilator parameter limit;

determining, by the processor, the at least one alarm setting limit based on the patient parameter, wherein the at least one alarm setting limit is different than the ventilator parameter limit;

comparing the alarm setting to the at least one alarm setting limit, wherein the at least one alarm setting limit is representative of at least one value for the ventilator parameter that is not to be exceeded based on the patient parameter;

determining whether the alarm setting exceeds the at least one alarm setting limit; and based on the determining operation, performing one of accepting the alarm setting or rejecting the alarm setting.

10. The method of claim 9, further comprising:

in response to determining that the alarm setting does not exceed the at least one alarm setting limit, accepting the alarm setting.

11. The method of claim 9, further comprising:

in response to determining that the alarm setting exceeds the at least one alarm setting limit, rejecting the alarm setting.

12. The method of claim 9, wherein the at least one alarm setting limit comprises at least one of: an upper alarm setting limit and a lower alarm setting limit.

13. The method of claim 9, wherein the at least one value is preset and included in the instructions of the memory.

14. The method of claim 9, wherein the at least one value is a function of the patient parameter.

15. The method of claim 9, wherein the at least one value is configured to prevent patient distress while allowing alarm settings to be customized for a particular patient.

16. A ventilator comprising a display device, the ventilator configured with a computer having a processor and a memory, the memory communicatively coupled to the processor and containing instructions that, when executed by the processor, cause the ventilator to provide a graphical user interface on the display device, the graphical user interface comprising:

a main setup screen, comprising:
　a first input element for receiving a patient ideal body weight;
　a second input element for receiving a ventilation strategy; and
　a third input element for receiving a ventilator parameter; and an alarm setup screen, comprising:
　an alarm button for receiving an alarm setting for the ventilator parameter, wherein the alarm setting is compared to at least one alarm setting limit, wherein the at least one alarm setting limit is automatically determined by the processor based on the received patient ideal body weight and the received ventilation strategy, and wherein the at least one alarm setting limit is different than a predetermined limit for the ventilator parameter; and
　a graphical alarm setting display, wherein the received alarm setting is accepted and displayed in the graphical alarm setting display if the alarm setting does not exceed the at least one alarm setting limit.

17. The ventilator of claim 16, wherein the received alarm setting is not accepted and is not displayed in the graphical alarm setting display if the alarm setting exceeds the at least one alarm setting limit.

18. The ventilator of claim 16, wherein the alarm setup screen further comprises:

a graphical element indicating that the alarm setting exceeds the at least one alarm setting limit.

19. The ventilator of claim 16, wherein the at least one alarm setting limit comprises at least one of: an upper alarm setting limit and a lower alarm setting limit.

20. The ventilator of claim 16, wherein the at least one alarm setting limit is configured to prevent patient distress while allowing alarm settings to be customized for a particular patient.

* * * * *